(12) United States Patent
Shadid et al.

(10) Patent No.: US 12,266,429 B2
(45) Date of Patent: Apr. 1, 2025

(54) INTEGRATED HEALTHCARE METHODS AND SYSTEMS

(71) Applicant: JPMorgan Chase Bank, N.A., New York, NY (US)

(72) Inventors: Noor Shadid, Wilmington, DE (US); Robert S. Newnam, Wilmington, DE (US); Ta-Wei Chen, Princeton Junction, NJ (US); Erin Michelle Perry, Townsend, DE (US); James P. White, III, Middletown, DE (US); Richard A. Hall, Marysville, OH (US); Mary Anderson, Delaware, OH (US)

(73) Assignee: JPMORGAN CHASE BANK, N.A., New York, NY (US)

( * ) Notice: Subject to any disclaimer, the term of this patent is extended or adjusted under 35 U.S.C. 154(b) by 532 days.

(21) Appl. No.: 17/036,671

(22) Filed: Sep. 29, 2020

(65) Prior Publication Data

US 2021/0098093 A1    Apr. 1, 2021

Related U.S. Application Data

(60) Provisional application No. 62/908,038, filed on Sep. 30, 2019.

(51) Int. Cl.
*G16H 10/60*    (2018.01)
*G16H 15/00*    (2018.01)
(Continued)

(52) U.S. Cl.
CPC ............ *G16H 10/60* (2018.01); *G16H 15/00* (2018.01); *G16H 20/10* (2018.01); *G16H 40/63* (2018.01); *G16H 40/67* (2018.01)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS

| | | | | |
|---|---|---|---|---|
| 2004/0030227 A1* | 2/2004 | Littrup | ..................... | A61N 7/02 600/300 |
| 2004/0094564 A1* | 5/2004 | Papp | ..................... | G06V 20/66 221/25 |

(Continued)

OTHER PUBLICATIONS

Patil et al. 2006, "Preliminary Design of Remotely Used and Monitored Medication Dispenser," 2006 International Conference of the IEEE Engineering in Medicine and Biology Society, 2006, pp. 3616-3619, doi: 10.1109/IEMBS.2006.260419.*

(Continued)

*Primary Examiner* — Robert W Morgan
*Assistant Examiner* — Charles P Coleman
(74) *Attorney, Agent, or Firm* — GREENBLUM & BERNSTEIN, P.L.C.

(57) ABSTRACT

Systems and methods are provided for integrated healthcare management. The systems and methods include establishing a medical record data, accessing information about a treatment related to the medical record data, obtaining biometric data related to the treatment, processing the biometric data, determining whether the treatment is appropriate with respect to the biometric data, in response to the treatment being appropriate with respect to the biometric data, administering medication, and in response the treatment not being appropriate with respect to the biometric data, determining a new treatment, and administering new medication based on the new treatment.

20 Claims, 13 Drawing Sheets

(51) Int. Cl.
*G16H 20/10* (2018.01)
*G16H 40/63* (2018.01)
*G16H 40/67* (2018.01)

(58) Field of Classification Search
CPC ........ G16H 20/17; G16H 30/00; G16H 40/00; G16H 50/00; G16H 70/00; G16H 80/00; G16H 10/60; G16H 40/67; G16H 40/63; G06Q 50/22–24
USPC .................................................. 705/3, 2, 20
See application file for complete search history.

(56) References Cited

U.S. PATENT DOCUMENTS

| | | | |
|---|---|---|---|
| 2011/0282489 A1* | 11/2011 | Buisman ................ | G16H 20/13 700/236 |
| 2012/0215157 A1* | 8/2012 | Berryman .............. | A61B 34/73 137/13 |
| 2017/0258332 A1* | 9/2017 | Wynn .................. | A61B 5/0095 |
| 2018/0233225 A1* | 8/2018 | Experton ............... | G16H 10/60 |
| 2018/0350455 A1* | 12/2018 | Rosen .................... | G16H 80/00 |
| 2019/0385741 A1* | 12/2019 | Anglada Cortes ..... | G16H 15/00 |
| 2020/0353173 A1* | 11/2020 | Holmquist .............. | A61M 5/20 |
| 2021/0106265 A1* | 4/2021 | Rau ....................... | A61B 5/4884 |
| 2022/0270733 A1* | 8/2022 | Hagen ................... | G16H 20/10 |
| 2022/0336074 A1* | 10/2022 | Bakos ................. | H04W 12/037 |
| 2022/0409127 A1* | 12/2022 | Albertini ............... | A61B 5/4839 |

OTHER PUBLICATIONS

El-Sappagh et al. 2019, "A mobile health monitoring-and-treatment system based on integration of the SSN sensor ontology and the HL7 FHIR standard," BMC Med Inform Decis Mak. May 10, 2019;19(1):97. doi: 10.1186/s12911-019-0806-z. PMID: 31077222; PMCID: PMC6511155.*

* cited by examiner

400

INTEGRATED HEALTHCARE METHODS AND SYSTEMS

CROSS-REFERENCE TO RELATED APPLICATIONS

This application claims the benefit of priority from U.S. Provisional Patent Application No. 62/908,038, filed Sep. 30, 2019, which is herein incorporated by reference in its entirety.

TECHNICAL FIELD

Example embodiments generally relate to integrated healthcare methods and systems. Specifically, example embodiment relate to methods and systems for managing and operating multi-product delivery platforms usable onsite.

BACKGROUND

Currently, it is typically difficult to deliver medication for patients that are not in a medical setting, patients being, e.g., on a worksite, on travel or on a battlefield. Also, patients are not always in a position to handle their medications properly, may not be willing and/or able to handle the medication properly, or may not be able to gather data about their current health, data that may be crucial in determining the type and medication that they need at any given time. Non-adherence to medication adds an additional $100 billion to $300 billion in health care costs, annually. In addition, medical data is typically not readily available to patients, and integration between various medical communities is currently not to the point of efficiently assisting a patient in determining the types and amounts of medication they may need at any given point in time, particularly when patients are not in a position to communicate with a medical center or facility. As a result, dispensing and distributing medicine to patients is typically expensive and difficult to manage, and tracking of the medicine dispensed to various patients is difficult as a result. In addition, treatment plans based on the current biometric data of individual patients are not always readily available, and proactive notifications on active health care emergency is not consistently available. Furthermore, dispensing drugs to specific individuals, and tracking the drugs that individual patients take is typically not completely accurate, and in general, tracking medication outside of a medical facility is a difficult process.

Therefore, there is a need for a portable multi-product delivery platform to deliver treatments and medicine directly to patients at the time they need it, as well as to track the medication and the real time biometric data of the patients. Furthermore, having data properly aggregated will assist in identifying trends, issues and blockers that will allow for continued improvements in overall adherence and compliance.

SUMMARY

The present disclosure, through one or more of its various aspects, embodiments, and/or specific features or sub-components, provides, inter alia, various systems, servers, devices, methods, media, programs, and platforms for providing an integrated healthcare system to deliver and track medication delivered to individual patients.

The various aspects, embodiments, features, and/or sub-components provide a multi-product delivery platform that includes a patch or similarly packaged devices as a system of delivery for treatment methods, including integral monitoring/tracking elements, telemetry elements (BLE, wireless, etc.), and personal identification elements. Thus, the various example embodiments provide an external control mechanism for configuration, data capture, monitoring/reporting, charging, scheduling, ordering, tracking and auditing real time biometric and healthcare information for individual patients.

In example embodiments, a method for managing integrated healthcare provides simplicity of process, security in the delivery of medical or treatment information to individual patients, end-to-end visibility of the process, real time feedback with respect to the ailment being treated and the treatment thereof, ease of distribution of the medication, and reduced cost.

According to an aspect of the present disclosure, a method for managing integrated healthcare is provided. The method is implemented by a processor on a computing device. The method includes: establishing, by the processor, a medical record data; accessing, by the processor, information about a treatment related to the medical record data; obtaining, by the processor, biometric data related to the treatment; processing, by the processor, the biometric data; determining, by the processor, whether the treatment is appropriate with respect to the biometric data; in response to the treatment being appropriate with respect to the biometric data, administering medication; and in response the treatment not being appropriate with respect to the biometric data: determining, by the processor, a new treatment; and administering new medication based on the determined new treatment.

According to another aspect of the present disclosure, the method may further include: receiving real-time feedback data corresponding to an efficacy of the first medication; determining a modified dosage level of the first medication based on the received real-time feedback data; and modifying the first information related to the first administration of the first medication based on the determined modified dosage level of the first medication.

According to a further aspect of the present disclosure, the method may further include: receiving real-time feedback data corresponding to an efficacy of the second medication; determining a modified dosage level of the second medication based on the received real-time feedback data; and modifying the second information related to the second administration of the second medication based on the determined modified dosage level of the second medication.

According to yet another aspect of the present disclosure, the medical record data may include one or more of the following data related to a patient who is undergoing the first treatment or the second treatment: medical history data of the patient, past ailments and diseases data related to the patient, data related to past treatments and procedures performed on the patient, current ailments and diseases data related to the patient, data related to current treatments and procedures being performed on the patient, diagnoses data for the patient's ailments, data related to types and amounts of medication that the patient has been prescribed in the past and is currently being prescribed, and data related to any allergies or adverse reactions to medications that the patient has, but the disclosure is not limited thereto.

According to a further aspect of the present disclosure, the biometric data may include one or more of the following data related to a patient who is undergoing the first treatment or the second treatment: data related to blood pressure of the patient, data related to heartbeat rhythm of the patient, and data related to glucose levels of the patient, data related to lipid panel of the patient, but the disclosure is not limited thereto.

According to another aspect of the present disclosure, the information about the first treatment may include one or more of the following data related to a patient who is undergoing the first treatment: data related to an amount of dosage of the first medication, data related to a timing of dispensation of the first medication to the patient, and data related to a manner in which the first medication is to be administered to the patient, but the disclosure is not limited thereto.

According to an additional aspect of the present disclosure, the information about second treatment may include one or more of the following data related to a patient who is undergoing the second treatment: data related to an amount of dosage of the second medication, data related to a timing of dispensation of the second medication to the patient, and data related to a manner in which the second medication is to be administered to the patient, but the disclosure is not limited thereto.

According to yet another aspect of the present disclosure, the method may further include: implementing drug dispensing safety check and control mechanism.

According to a further aspect of the present disclosure, the method may further include: defining verifiable operation range of safety parameters or properties including drug combination and dosage concentrations related to the biometric data; ingesting data input from various sources including health care team, electronic records, market participants and government, and transforming all external inputs to formulated logical constraints, and passing the logical constraints through satisfiability modulo theory solver against the safety parameters or properties to determine whether the control mechanism is to be activated, wherein the wherein the activation of the control mechanism is based on two factor authentication or two factor validation.

According to yet another aspect of the present disclosure, wherein when the control mechanism is activated, the method may further include: controlling dispensing amount of the first medication or the second medication.

According to a further aspect of the present disclosure, wherein when the control mechanism is activated, the method may further include: monitoring biometric data of a patient in real time; and interfacing with the patient's healthcare provider computing device and medication inventory computing device to administer the appropriate type and amount of medication to the patient that are appropriate given the patient's current health state in real time.

According to another aspect of the present disclosure, a computing device configured to implement an execution of a method for managing integrated healthcare is provided. The computing device includes a display screen, a processor, a memory, and a communication interface coupled to each of the processor, the memory, and the display screen. When the method is being executed, the processor is configured to: establish a medical record data; access information about a treatment related to the medical record data; obtain biometric data related to the treatment; process the biometric data; determine whether the treatment is appropriate with respect to the biometric data; administer medication in response to the treatment being appropriate with respect to the biometric data; and in response the treatment not being appropriate with respect to the biometric data: determine a new treatment; and administer new medication based on the determined new treatment.

According to yet another aspect of the present disclosure, the processor may be further configured to: receive real-time feedback data corresponding to an efficacy of the first medication; determine a modified dosage level of the first medication based on the received real-time feedback data; and modify the first information related to the first administration of the first medication based on the determined modified dosage level of the first medication.

According to a further aspect of the present disclosure, the processor may be further configured to: receive real time feedback data corresponding to an efficacy of the second medication; determine a modified dosage level of the second medication based on the received real-time feedback data; and modify the second information related to the second administration of the second medication based on the determined modified dosage level of the second medication.

According to yet another aspect of the present disclosure, the processor may be further configured to: implement drug dispensing safety check and control mechanism.

According to a further aspect of the present disclosure, the processor may be further configured to: define verifiable operation range of safety parameters or properties including drug combination and dosage concentrations related to the biometric data; ingest data input from various sources including health care team, electronic records, market participants and government, and transform all external inputs to formulated logical constraints; and pass the logical constraints through satisfiability modulo theory solver against the safety parameters or properties to determine whether the control mechanism is to be activated, wherein the wherein the activation of the control mechanism is based on two factor authentication or two factor validation.

According to yet another aspect of the present disclosure, wherein when the control mechanism is activated, the processor may be further configured to: control dispensing amount of the first medication or the second medication.

According to a further aspect of the present disclosure, wherein when the control mechanism is activated, the processor may be further configured to: monitor biometric data of a patient in real time; and interface with the patient's healthcare provider computing device and medication inventory computing device to administer the appropriate type and amount of medication to the patient that are appropriate given the patient's current health state in real time.

According to another aspect of the present disclosure, a non-transitory computer readable medium configured to store instructions for integrated healthcare management implemented by a processor on a sensor-equipped computing device is disclosed. The instructions, when executed, may cause a processor to perform the following: generating a medical record data, accessing information about a first treatment related to the medical record data; obtaining, by the sensor and validated by the processor, biometric data related to the first treatment; processing the biometric data; determining whether the first treatment is appropriate with respect to the biometric data; in response to the first treatment being appropriate with respect to the biometric data, outputting first information related to a first administration of a first medication; and in response to the first treatment not being appropriate with respect to the biometric data: determining a second treatment; and outputting second information related to a second administration of a second medication based on the determined second treatment.

BRIEF DESCRIPTION OF THE DRAWINGS

The present disclosure is further described in the detailed description which follows, in reference to the noted plurality of drawings, by way of non-limiting examples of preferred embodiments of the present disclosure, in which like characters represent like elements throughout the several views of the drawings.

DETAILED DESCRIPTION

Figure 1:
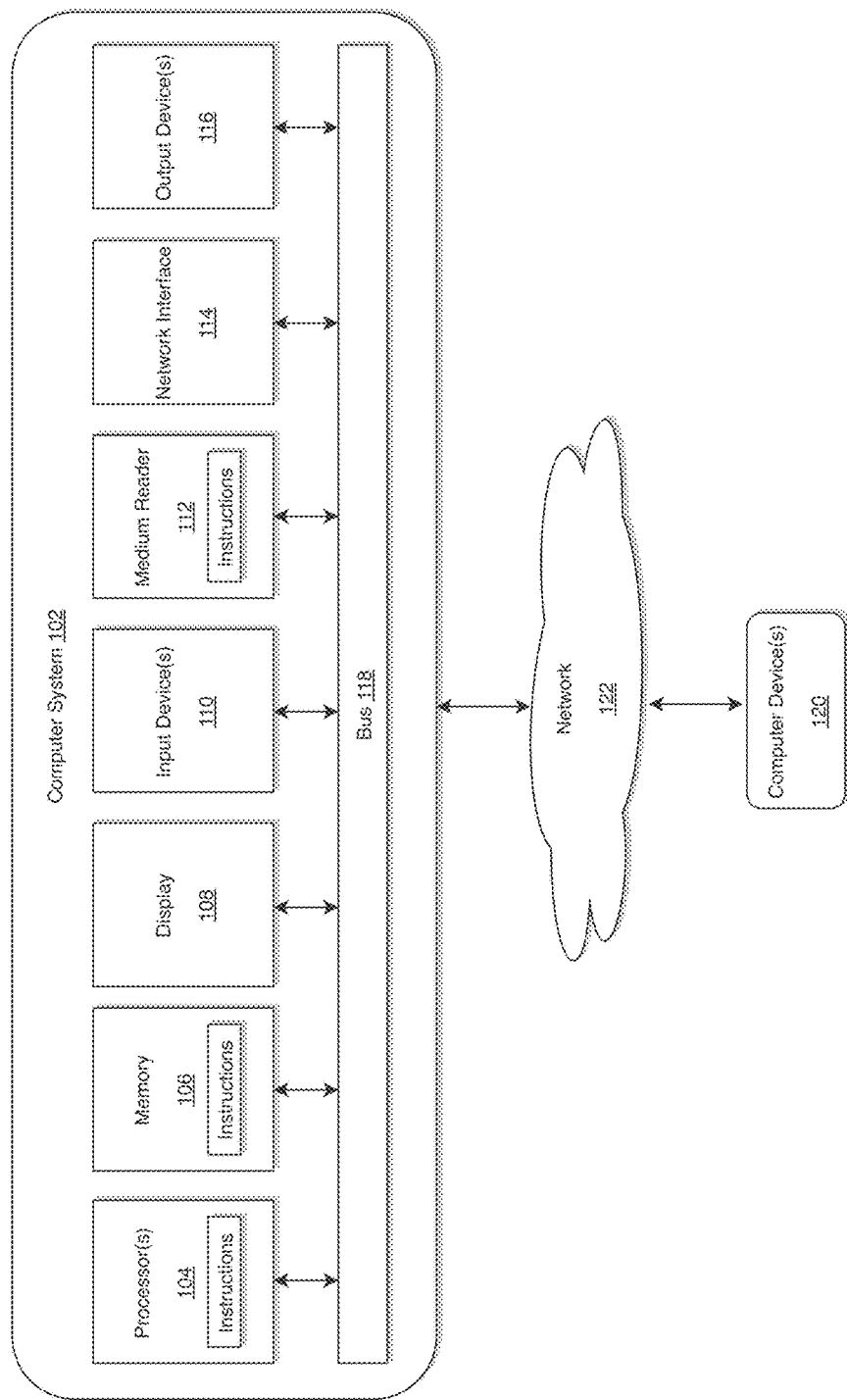
FIG. 1 illustrates a computer system for implementing integrated healthcare management, according to an example embodiment.

Through one or more of its various aspects, embodiments and/or specific features or sub-components of the present disclosure, are intended to bring out one or more of the advantages as specifically described above and noted below.

Specifically, example methods and systems provide integrated healthcare management to allow for the timely and accurate delivery of needed medication to individual patients in a variety of circumstances, as described below.

The examples may also be embodied as one or more non-transitory computer readable media having instructions stored thereon for one or more aspects of the present technology as described and illustrated by way of the examples herein. The instructions in some examples include executable code that, when executed by one or more processors, cause the processors to carry out steps necessary to implement the methods of the examples of this technology that are described and illustrated herein.

As is traditional in the field of the present disclosure, example embodiments are described, and illustrated in the drawings, in terms of functional blocks, units and/or modules. Those skilled in the art will appreciate that these blocks, units and/or modules are physically implemented by electronic (or optical) circuits such as logic circuits, discrete components, microprocessors, hard wired circuits, memory elements, wiring connections. and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the example embodiments may be physically separated into two or more interacting and discrete blocks, units and/or modules without departing from the scope of the inventive concepts. Further, the blocks, units and/or modules of the example embodiments may be physically combined into more complex blocks, units and/or modules without departing from the scope of the present disclosure.

FIG. 1 is an example integrated healthcare management (IHM) system for use in accordance with the embodiments described herein. The integrated healthcare management (IHM) system 100 is generally shown and may include a computer system 102, which is generally indicated.

The computer system 102 may include a set of instructions that can be executed to cause the computer system 102 to perform any one or more of the methods or computer based functions disclosed herein, either alone or in combination with the other described devices. The computer system 102 may operate as a standalone device or may be connected to other systems or peripheral devices. For example, the computer system 102 may include, or be included within, any one or more computers, servers, systems, communication networks or cloud environment. Even further, the instructions may be operative in such cloud-based computing environment.

In a networked deployment, the computer system 102 may operate in the capacity of a server or as a client user computer in a server-client user network environment, a client user computer in a cloud computing environment, or as a peer computer system in a peer-to-peer (or distributed) network environment. The computer system 102, or portions thereof, may be implemented as, or incorporated into, various devices, such as a personal computer, a tablet computer, a set-top box, a personal digital assistant, a mobile device, a palmtop computer, a laptop computer, a desktop computer, a communications device, a wireless smart phone, a personal trusted device, a wearable device, a global positioning satellite (GPS) device, a web appliance, or any other machine capable of executing a set of instructions (sequential or otherwise) that specify actions to be taken by that machine. Further, while a single computer system 102 is illustrated, additional embodiments may include any collection of systems or sub-systems that individually or jointly execute instructions or perform functions. The term "system" shall be taken throughout the present disclosure to include any collection of systems or sub-systems that individually or jointly execute a set, or multiple sets, of instructions to perform one or more computer functions.

As illustrated in FIG. 1, the computer system 102 may include at least one processor 104. The processor 104 is tangible and non-transitory. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. The processor 104 is an article of manufacture and/or a machine component. The processor 104 is configured to execute software instructions in order to perform functions as described in the various embodiments herein. The processor 104 may be a general purpose processor or may be part of an application specific integrated circuit (ASIC). The processor 104 may also be a microprocessor, a microcomputer, a processor chip, a controller, a microcontroller, a digital signal processor (DSP), a state machine, or a programmable logic device. The processor 104 may also be a logical circuit, including a programmable gate array (PGA) such as a field programmable gate array (FPGA), or another type of circuit that includes discrete gate and/or transistor logic. The processor 104 may be a central processing unit (CPU), a graphics processing unit (GPU), or both. Additionally, any processor described herein may include multiple processors, parallel processors, or both. Multiple processors may be included in, or coupled to, a single device or multiple devices.

The computer system 102 may also include a computer memory 106. The computer memory 106 may include a static memory, a dynamic memory, or both in communication. Memories described herein are tangible storage mediums that can store data and executable instructions, and are non-transitory during the time instructions are stored therein. Again, as used herein, the term "non-transitory" is to be interpreted not as an eternal characteristic of a state, but as a characteristic of a slate that will last for a period of time. The term "non-transitory" specifically disavows fleeting characteristics such as characteristics of a particular carrier wave or signal or other forms that exist only transitorily in any place at any time. The memories are an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a cache, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted. Of course, the computer memory 106 may comprise any combination of memories or a single storage.

The computer system 102 may further include a display 108, such as a liquid crystal display (LCD), an organic light emitting diode (OLED), a flat panel display, a solid state display, a cathode ray tube (CRT), a plasma display, or any other type of display, examples of which are well known to skilled persons.

The computer system 102 may also include at least one input device 110, such as a keyboard, a touch-sensitive input screen or pad, a speech input, a mouse, a remote control device having a wireless keypad, a microphone coupled to a speech recognition engine, a camera such as a video camera or still camera, a cursor control device, a global positioning system (GPS) device, an altimeter, a gyroscope, an accelerometer, a proximity sensor, or any combination thereof. Those skilled in the art appreciate that various embodiments of the computer system 102 may include multiple input devices 110. Moreover, those skilled in the art further appreciate that the above-listed, exemplary input devices 110 are not meant to be exhaustive and that the computer system 102 may include any additional, or alternative, input devices 110.

The computer system 102 may also include a medium reader 112 which is configured to read any one or more sets of instructions, e.g. software, from any of the memories described herein. The instructions, when executed by a processor, can be used to perform one or more of the methods and processes as described herein. In a particular embodiment, the instructions may reside completely, or at least partially, within the memory 106, the medium reader 112, and/or the processor 110 during execution by the computer system 102.

Furthermore, the computer system 102 may include any additional devices, components, parts, peripherals, hardware, software or any combination thereof which are commonly known and understood as being included with or within a computer system, such as, but not limited to, a network interface 114 and an output device 116. The output device 116 may be, but is not limited to, a speaker, an audio out, a video out, a remote control output, a printer, or any combination thereof.

Each of the components of the computer system 102 may be interconnected and communicate via a bus 118 or other communication link. As shown in FIG. 1, the components may each be interconnected and communicate via an internal bus. However, those skilled in the art appreciate that any of the components may also be connected via an expansion bus. Moreover, the bus 118 may enable communication via any standard or other specification commonly known and understood such as, but not limited to, peripheral component interconnect, peripheral component interconnect express, parallel advanced technology attachment, serial advanced technology attachment, etc.

The computer system 102 may be in communication with one or more additional computer devices 120 via a network 122. The network 122 may be, but is not limited to, a local area network, a wide area network, the Internet, a telephony network, a short-range network, or any other network commonly known and understood in the art. The short-range network may include, for example. Bluetooth, Zigbee, infrared, near field communication, ultraband, or any combination thereof. Those skilled in the art appreciate that additional networks 122 which are known and understood may additionally or alternatively be used and that the exemplary networks 122 are not limiting or exhaustive. Also, while the network 122 is shown in FIG. 1 as a wireless network, those skilled in the art appreciate that the network 122 may also be a wired network.

The additional computer device 120 is shown in FIG. 1 as a personal computer. However, those skilled in the art appreciate that, in alternative embodiments of the present application, the computer device 120 may be a laptop computer, a tablet PC, a personal digital assistant, a mobile device, a palmtop computer, a desktop computer, a communications device, a wireless telephone, a personal trusted device, a web appliance, a server, or any other device that is capable of executing a set of instructions, sequential or otherwise, that specify actions to be taken by that device. Of course, those skilled in the art appreciate that the above-listed devices are merely exemplary devices and that the device 120 may be any additional device or apparatus commonly known and understood in the art without departing from the scope of the present application. For example, the computer device 120 may be the same or similar to the computer system 102. Furthermore, those skilled in the art similarly understand that the device may be any combination of devices and apparatuses.

Of course, those skilled in the art appreciate that the above-listed components of the computer system 102 are merely meant to be exemplary and are not intended to be exhaustive and/or inclusive. Furthermore, the examples of the components listed above are also meant to be exemplary and similarly are not meant to be exhaustive and/or inclusive.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

Figure 2:
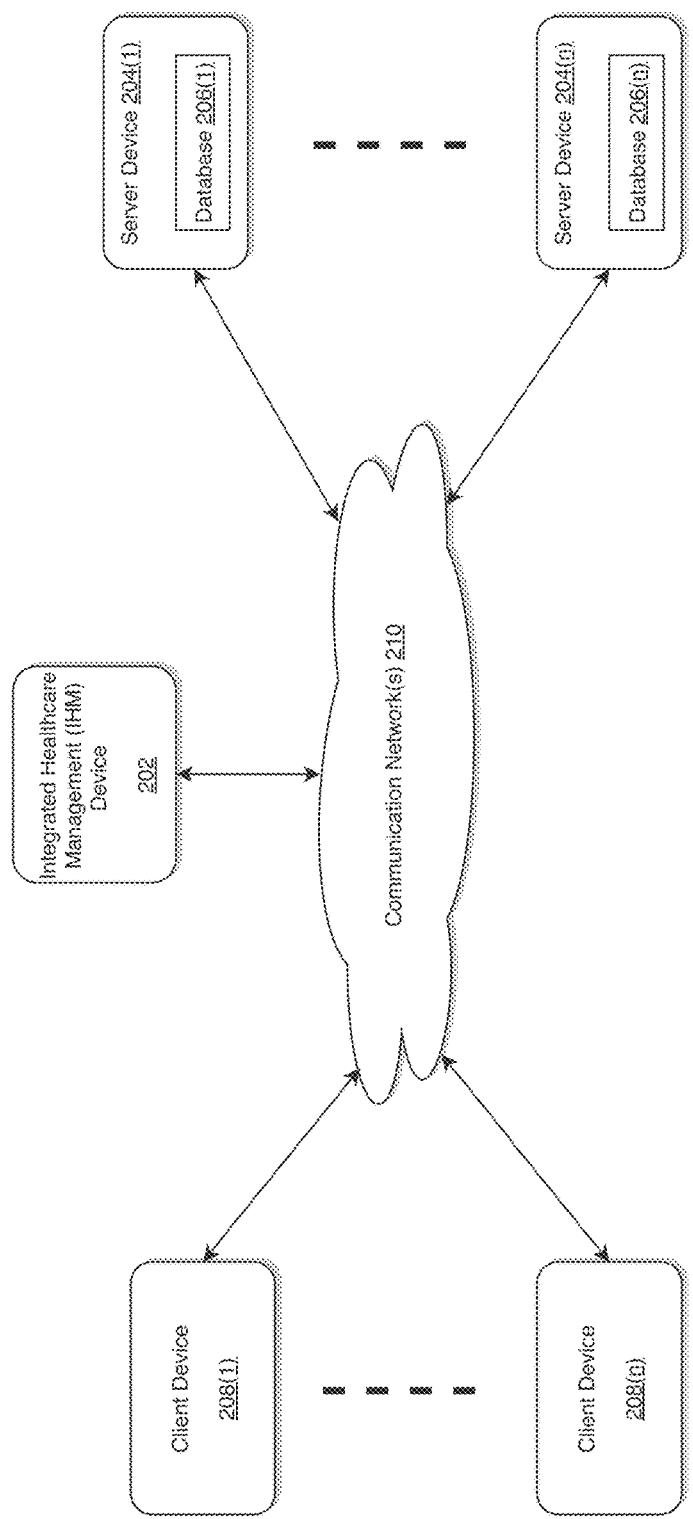
FIG. 2 illustrates a diagram of a network environment for integrated healthcare management, according to an example embodiment.

Referring to FIG. 2, a schematic of an exemplary network environment 200 for implementing integrated healthcare management is illustrated. In an exemplary embodiment, the integrated healthcare management framework is executable on any networked computer platform, such as, for example, a wireless mobile communication device, i.e., a smart phone.

The Integrated Healthcare Management (IHM) device 202 may be the same or similar to the computer system 102 as described with respect to FIG. 1. The IHM device 202 may store one or more applications that can include executable instructions that, when executed by the IHM device 202, cause the IHM device 202 to perform actions, such as to transmit, receive, or otherwise process network messages, for example, and to perform other actions described and illustrated below with reference to the figures. The application(s) may be implemented as modules or components of other applications. Further, the application(s) can be implemented as operating system extensions, modules, plugins, or the like.

Even further, the application(s) may be operative in a cloud-based computing environment. The application(s) may be executed within or as virtual machine(s) or virtual server(s), or through a collection of micro-services that may be managed in a cloud-based computing environment. Also, the application(s) and some non-real time analytical functions performed by the IHM device 202 itself, may be located in virtual server(s) running in a cloud-based computing environment rather than being tied to one or more specific physical network computing devices. Also, the application(s) may be running in one or more virtual machines (VMs) executing on the IHM device 202. Additionally, in one or more embodiments of this technology, virtual machine(s) or micro-services running on the IHM device 202 may be managed or supervised by a hypervisor or service orchestration functions.

In the network environment 200 of FIG. 2, the IHM device 202 is coupled to a plurality of server devices 204(1)-204(n) that hosts a plurality of databases 206(1)-206(n), and also to a plurality of client devices 208(1)-208(n) via communication network(s) 210. A communication interface of the IHM device 202, such as the network interface 114 of the computer system 102 of FIG. 1, operatively couples and communicates between the IHM device 202, the server devices 204(1)-204(n), and/or the client devices 208(1)-208(n), which are all coupled together by the communication network(s) 210, although other types and/or numbers of communication networks or systems with other types anti/or numbers of connections and/or configurations to other devices and/or elements may also be used.

The communication network(s) 210 may be the same or similar to the network 122 as described with respect to FIG. 1, although the IHM device 202, the server devices 204(1)-204(n), and/or the client devices 208(1)-208(n) may be coupled together via other topologies. Additionally, the network environment 200 may include other network devices such as one or more routers and/or switches, for example, which are well known in the art and thus will not be described herein. This technology provides a number of advantages including methods, non-transitory computer readable media, and integrated healthcare management devices that efficiently manage healthcare integration.

By way of example only, the communication network(s) 210 may include local area network(s) (LAN(s)) or wide area network(s) (WAN(s)), and can use TCP/IP over Ethernet and industry-standard transmission media and protocols, although other types and/or numbers of protocols and/or communication networks may be used. The communication network(s) 210 in this example may employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like.

The IHM device 202 may be a standalone device or integrated with one or more other devices or apparatuses, such as one or more of the server devices 204(1)-204(n), for example. In one particular example, the IHM device 202 may include or be hosted by one of the server devices 204(1)-204(n), and other arrangements are also possible. Moreover, one or more of the devices of the IHM device 202 may be in a same or a different communication network including one or more public, private, or cloud networks, for example.

The plurality of server devices 204(1)-204(n) may be the same or similar to the computer system 102 or the computer device 120 as described with respect to FIG. 1, including any features or combination of features described with respect thereto. For example, any of the server devices 204(1)-204(n) may include, among other features, one or more processors, a memory, and a communication interface, which are coupled together by a bus or other communication link, although other numbers and/or types of network devices may be used. The server devices 204(1)-204(n) in this example may process requests received from the IHM device 202 via the communication network(s) 210 according to the HTTP-based and/or JavaScript Object Notation (JSON) protocol, for example, although other protocols may also be used.

The server devices 204(1)-204(n) may be hardware or software or may represent a system with multiple servers in a pool, which may include internal or external networks. The server devices 204(1)-204(n) hosts the databases 206(1)-206(n) that are configured to store patient health data, medication data, and treatment data.

Although the server devices 204(1)-204(n) are illustrated as single devices, one or more actions of each of the server devices 204(1)-204(n) may be distributed across one or more distinct network computing devices that together comprise one or more of the server devices 204(1)-204(n). Moreover, the server devices 204(1)-204(n) are not limited to a particular configuration. Thus, the server devices 204(1)-204(n) may contain a plurality of network computing devices that operate using a master/slave approach, whereby one of the network computing devices of the server devices 204(1)-204(n) operates to manage and/or otherwise coordinate operations of the other network computing devices.

The server devices 204(1)-204(n) may operate as a plurality of network computing devices within a cluster architecture, a peer-to peer architecture, virtual machines, or within a cloud architecture, for example. Thus, the technology disclosed herein is not to be construed as being limited to a single environment and other configurations and architectures are also envisaged.

The plurality of client devices 208(1)-208(n) may also be the same or similar to the computer system 102 or the computer device 120 as described with respect to FIG. 1, including any features or combination of features described with respect thereto. For example, the client devices 208(1)-208(n) in this example may include any type of computing device that can facilitate the integration of healthcare management. Accordingly, the client devices 208(1)-208(n) may be mobile computing devices, desktop computing devices, laptop computing devices, tablet computing devices, virtual machines (including cloud-based computers), or the like, that host chat, e-mail, or voice-to-text applications, for example. In an exemplary embodiment, at least one client device 208 is a wireless mobile communication device, i.e., a smart phone.

The client devices 208(1)-208(n) may run interface applications, such as standard web browsers or standalone client applications, which may provide an interface to communicate with the IHM device 202 via the communication network(s) 210 in order to communicate user requests. The client devices 208(1)-208(n) may further include, among other features, a display device, such as a display screen or touchscreen, and/or an input device, such as a keyboard, for example.

Although the exemplary network environment 200 with the IHM device 202, the server devices 204(1)-204(n), the client devices 208(1)-208(n), and the communication network(s) 210 are described and illustrated herein, other types and/or numbers of systems, devices, components, and/or elements in other topologies may be used. It is to be understood that the systems of the examples described herein are for exemplary purposes, as many variations of the specific hardware and software used to implement the examples are possible, as will be appreciated by those skilled in the relevant art(s).

One or more of the devices depicted in the network environment 200, such as the IHM device 202, the server devices 204(1)-204(n), or the client devices 208(1)-208(n), for example, may be configured to operate as virtual instances on the same physical machine. In other words, one or more of the IHM device 202, the server devices 204(1)-204(n), or the client devices 208(1)-208(n) may operate on the same physical device rather than as separate devices communicating through communication network(s) 210. Additionally, there may be more or fewer IHM devices 202, server devices 204(1)-204(n), or client devices 208(1)-208(n) than illustrated in FIG. 2.

In addition, two or more computing systems or devices may be substituted for any one of the systems or devices in any example. Accordingly, principles and advantages of distributed processing, such as redundancy and replication also may be implemented, as desired, to increase the robustness and performance of the devices and systems of the examples. The examples may also be implemented on computer system(s) that extend across any suitable network using any suitable interface mechanisms and traffic technologies, including by way of example only teletraffic in any suitable form (e.g., voice and modem), wireless traffic networks, cellular traffic networks, Packet Data Networks (PDNs), the Internet, intranets, and combinations thereof.

Figure 3:
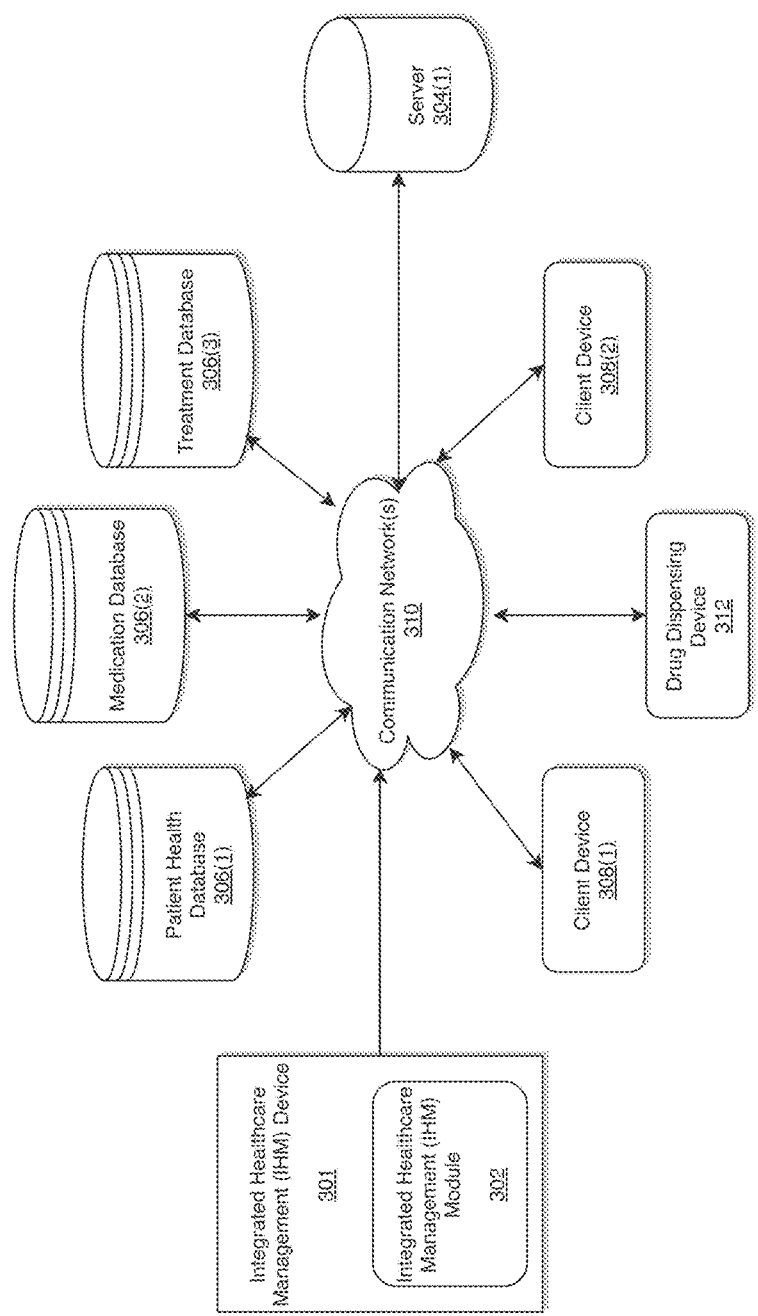
FIG. 3 shows a system for implementing integrated healthcare management, according to an example embodiment.

The IHM device 301 is described and shown in FIG. 3 as including an Integrated Healthcare Management (IHM) module 302, although it may include other rules, policies, modules, databases, or applications, for example. As will be described below, the IHM module 302 is configured to retrieve information from the patient health database 306(1), the medication database 306(2) and the treatment database 306(3) generate instructions to deliver specific types and amounts of medications to specific individuals and manage the delivery of the medications to each of the individuals.

According to exemplary embodiments, the IHM device 301, the patient health database 306(1), the medication database 306(2), the treatment database 306(3), the first client device 308(1), the second client device 308(2), the server 304(1), and the network 310 as illustrated in FIG. 3 may be the same or similar to the IHM device 202, the database 206(1), the database 206(2), the database 206(3), the first client device 208(1), the second client device 208(2), the server 204(1), and the network 210, respectively, as illustrated in FIG. 2.

An exemplary process 300 for implementing an integrated healthcare management framework by utilizing the network environment of FIG. 2 is shown as being executed in FIG. 3. Specifically, a first client device 308(1) and a second client device 308(2) are illustrated as being in communication with IHM device 301. In this regard, the first client device 308(1) and the second client device 308(2) may be "clients" of the IHM device 301 and are described herein as such. Nevertheless, it is to be known and understood that the first client device 308(1) and/or the second client device 308(2) need not necessarily be "clients" of the IHM device 301, or any entity described in association therewith herein. Any additional or alternative relationship may exist between either or both of the first client device 308(1) and the second client device 308(2) and the IHM device 301, or no relationship may exist.

Further, IHM device 301 is illustrated as being able to access the patient health database 306(1), the medication database 306(2) and the treatment database 306(3). The IHM module 302 may be configured to access these databases for implementing an integrated healthcare management framework.

The first client device 308(1) may be, for example, a smart phone, a personal computer (PC) or a wearable device such as a wearable sensor configured to transmit biometric data to the IHM device 301 and to receive instructions from the IHM device 301. Of course, the first client device 308(1) may be any additional device described herein. The second client device 308(2) may be, for example, a PC or a wearable device such as a wearable sensor configured to transmit biometric data to the IHM device 301 and to receive instructions from the IHM device 301. Of course, the second client device 308(2) may also be any additional device described herein.

The process may be executed via the communication network(s) 310, which may comprise plural networks as described above. For example, in an exemplary embodiment, either or both of the first client device 308(1) and the second client device 308(2) may communicate with the IHM device 301 via broadband or cellular communication. Of course, these embodiments are merely exemplary and are not limiting or exhaustive.

Figure 3A:
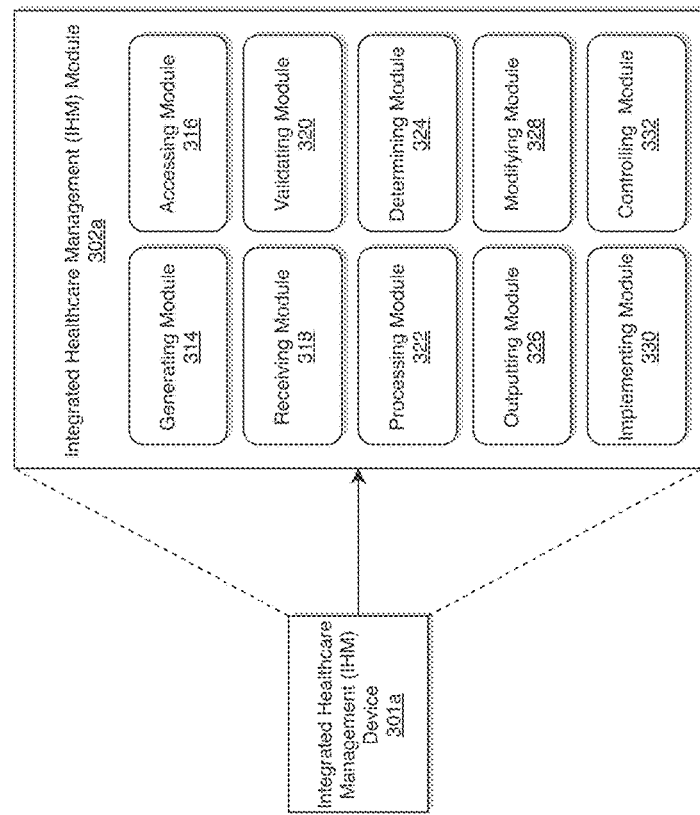
FIG. 3A shows a system for implementing integrated healthcare management device having an integrated healthcare management module of FIG. 3, according to an example embodiment.

FIG. 3A shows a system tor implementing integrated healthcare management device having an integrated healthcare management module of FIG. 3, according to an example embodiment. As illustrated in FIG. 3A, an IHM module 302a may be embedded within an IHM device 301a. According exemplary embodiments, the IHM module 302a and the IHM device 301a as illustrated in FIG. 3A may be the same or similar to the IHM module 302 and the IHM device 301, respectively, as illustrated in FIG. 3.

The IHM module 302a may include a generating module 314, an accessing module 316, a receiving module 318, a validating module 320, a processing module 322, a determining module 324, an outputting module 326, a modifying module 328, an implementing module 330, and a controlling module 332.

According to exemplary embodiments, each of the generating module 314, accessing module 316, receiving module 318, validating module 320, processing module 322, determining module 324, outputting module 326, modifying module 328, implementing module 330, and the controlling module 332 may be implemented by microprocessors or similar, they may be programmed using software (e.g., microcode) to perform various functions discussed herein and may optionally be driven by firmware and/or software. Alternatively, each of the generating module 314, accessing module 316, receiving module 318, validating module 320, processing module 322, determining module 324, outputting module 326, modifying module 328, implementing module 330, and the controlling module 332 may be implemented by dedicated hardware, or as a combination of dedicated hardware to perform some functions and a processor (e.g., one or more programmed microprocessors and associated circuitry) to perform other functions. Also, according to exemplary embodiments, each of the generating module 314, accessing module 316, receiving module 318, validating module 320, processing module 322, determining module 324, outputting module 326, modifying module 328, implementing module 330, and the controlling module 332 may be physically separated into two or more interacting and discrete blocks, units, devices, and/or modules without departing from the scope of the inventive concepts.

According to exemplary embodiments, the IHM module 302a may be configured to implement an integrated healthcare management process by utilizing a processor on sensor-equipped computing device. For example, the generating module 314 of the IHM module 302a may be configured to generate a medical record data related to a patient. The accessing module 316 may be configured to access information about a first treatment related to the medical record data. The receiving module 318 may be configured to obtain, by utilizing the sensor and validated by the validating module 320, biometric data related to the first treatment. The processing module 322 may be configured to process the biometric data and the determining module 324 may be configured to determine whether the first treatment is appropriate with respect to the biometric data.

When the determining module 324 determines that the first treatment is appropriate with respect to the biometric data, the outputting module 326 may output first information related to a first administration of a first medication.

When the determining module 324 determines that the first treatment is not appropriate with respect to the biometric data, the determining module further determines a second treatment and the outputting module outputs second information related to a second administration of a second medication based on the determined second treatment.

According to exemplary embodiments, the receiving module 318 may be configured to receive real-time feedback data corresponding to an efficacy of the first medication, the determining module 324 may further determine a modified dosage level of the first medication based on the received real-time feedback data, and the modifying module 328 may modify the first information related to the first administration of the first medication based on the determined modified dosage level of the first medication.

Alternatively, according to exemplary embodiments, the receiving module 318 may be configured to receive real-time feedback data corresponding to an efficacy of the second medication; the determining module 324 may further determine a modified dosage level of the second medication based on the received real-time feedback data; and the modifying module 328 may modify the second information related to the second administration of the second medication based on the determined modified dosage level of the second medication.

Upon being started, the IHM module 302 or 302a executes a process for integrated healthcare management. An exemplary process for implementing an integrated healthcare management is generally indicated at flowchart 400 in FIG. 4.

Figure 4:
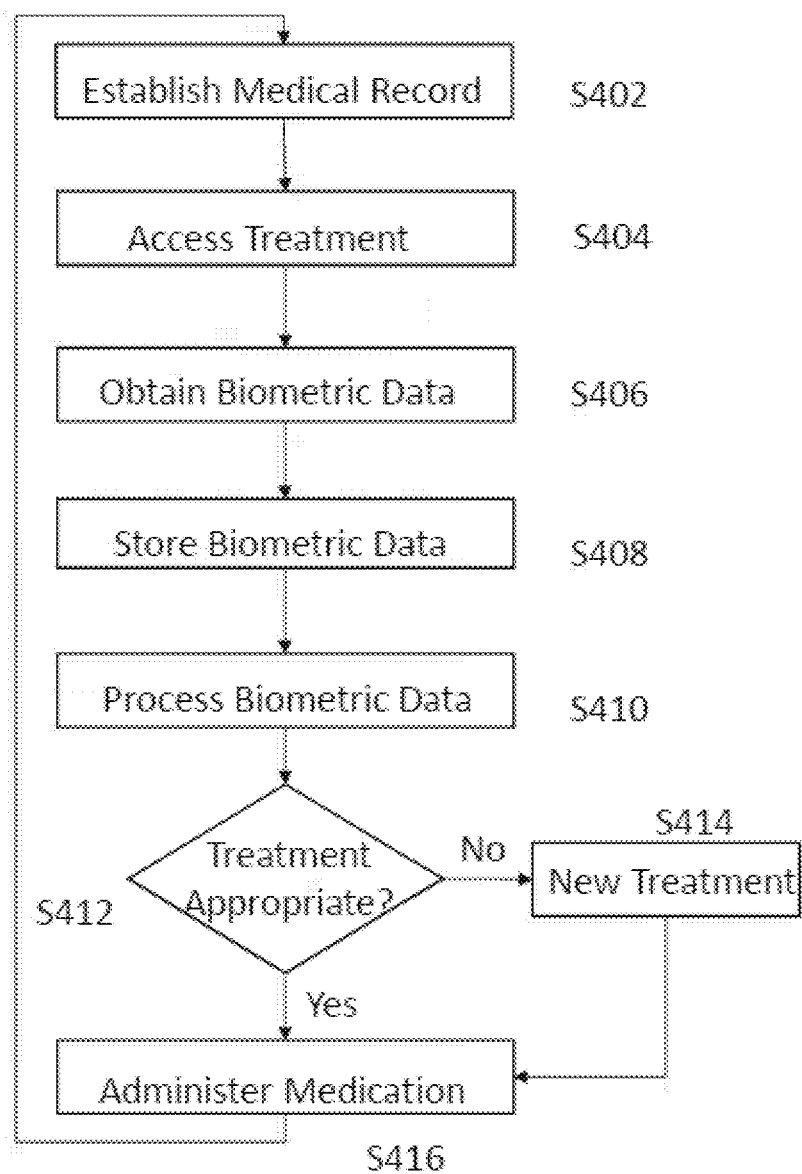
FIG. 4 is a flowchart of a process for integrated healthcare management, according to an example embodiment.

FIG. 4 is a flowchart illustrating a process for integrated healthcare management, according to an example embodiment. In the process 400 of FIG. 4, at step S402, the IHM module 302 establishes a medical record data for a patient. For example, the medical record data may include data related to a medical history of the patient, past ailments and diseases, past treatments and procedures performed on the patient, current ailments and diseases, current treatments and procedures, diagnoses for the patient's ailments, types and amounts of medication that five patient has been prescribed in the past and is currently being prescribed, any allergies or adverse reactions to medications that the patient may have, if any, and the like. In example embodiments, the medical record data is stored in one or more memories such as, e.g., the patient health database 306(1), the medication database 306(2) and/or the treatment database 306(3) illustrated in FIG. 3.

At step S404, in example embodiments, the IHM module 302 accesses treatment information for the patient at, for example, the treatment database 306(3), the treatment having been established by a medical professional such as, e.g., a doctor or a nurse practitioner at step S402. In example embodiments, the treatment information includes relevant information and treatment recommendations about a current treatment to which the patient is subjected such as, e.g., the amount of dosage of medication, timing of the dispensation of the medication to the patient, and manner in which the medication is to be administered to the patient.

At step S406, the IHM module 302 obtains real time biometric data about the patient. In an example embodiment, a biometric data gathering device is attached or otherwise operationally coupled to the patient, and is configured to collect biometric data of the patient such as, e.g., blood pressure, heartbeat rhythm, glucose levels, and the like. In example embodiments, the biometric data gathering device includes a wearable device, such as a watch or other device, that is attached or otherwise sufficiently close to the body of the patient to detect and gather the biometric data. In example embodiments, the biometric information gathering device includes a non-contact sensing device such as, e.g., an optical sensing device configured to extract remote vibration sources, or rotating linearly polarized light, by specific materials exposed to a magnetic field. In example embodiments, the biometric data gathering device includes a device configured to be in contact with the body of the patient, or that includes one or more sensors inside the skin of the patient. For example, the biometric data gathering device may include a micro-assay attached to the body of the patient. Although specific examples of biometric data gathering devices are discussed above, any other portable biometric data gathering device, available currently or in the future, contact or non-contact, outside of the patient's body or inside the patient's body, may be used to gather biometric data about the patient at step S406.

In example embodiments, at step S408, the patient health database 306(1), the medication database 306(2) and the treatment database 306(3) receive the patient biometric data gathered at step S406. For example, with reference to FIG. 3, the IHM module 302 transmits and stores the biometric data at, e.g., the patient health database 306(1), the medication database 306(2) and the treatment database 306(3).

In example embodiments, at step S410, the IHM module 302 processes the received biometric data received at step S406 and stored at step S408. In example embodiments, the IHM module 302 retrieves the medical record data and the treatment information of the patient that was obtained at steps S402 and S404, and compares the treatment information with the stored current biometric data to determine whether the treatment information is compatible with the current biometric data of the patient. Specifically, the IHM module 302 determines whether the treatment recommendation included in the treatment information is appropriate for the patient given the current health state of the patient given by the current biometric data of the patient.

In example embodiments, at step S412, the IHM module 302 determines whether the treatment recommendations accessed at step S404 are appropriate with respect to the collected current biometric data of the patient. In example embodiments, if the treatment recommendations are not appropriate given the collected biometric data of the patient, then at step S414 the IHM module 302 modifies the treatment recommendations to generate a new treatment that is better suited to address any ailment derived from the collected biometric data of the patient. Specifically, the IHM module 302 generates new treatment recommendations that are appropriate given the collected biometric data of the patient at step S414 and/or medical professional's input. In example embodiments, the IHM module 302 also updates the databases 306(1)-306(3) with the new treatment recommendations. When the new treatment recommendations, which are appropriate given the collected biometric data of the patient, have been generated, the IHM module 302 continues to step S416. In example embodiments, if at step S412, the IHM module 302 determines that the treatment recommendations accessed at step S404 are appropriate given the biometric data of the patient collected at step S406, then the IHM module 302 continues to step S416.

At step S416, in example embodiments, the IHM module 302 transmits the treatment information to the patient via, e.g., a mobile device of the patient. In example embodiments, the mobile device may be a smart phone, a tablet, a smart watch, or any other device configured to receive information wirelessly at the location of the patient. In example embodiments, the mobile device may be functionally coupled to a medication dispensing device that is configured to dispense the medication to the patient based on the treatment information provided by the IHM module 302 to the mobile device. For example, the medication dispensing device may include a syringe permanently or semi-permanently inserted into the patient's skin and configured to administer the appropriate dosage of medication to the patient intravenously. However, other medication dispensing devices may be used such as, e.g., oral dispensing devices, and the like.

In example embodiments, subsequently to step S412 or step S414, the IHM module 302 incorporates the appropriate treatment information to the record of the patient, and the medical record data of the patient is updated to include the latest treatment information and recommendations. Specifically, the IHM module 302 transmits the treatment information that is based on the collected biometric data back to the patient health database 306(1), the medication database 306(2) and the treatment database 306(3).

Referring back to FIG. 3A, according to exemplary embodiments, the IHM 302a may implement drug dispensing safety check and control mechanism. For example, the implementing module 330 and the controlling module 332 may be configured to implement drug dispensing safety check and control mechanism that may include: defining verifiable operation range of safety parameters or properties including drug combination and dosage concentrations related to the biometric data; ingesting data input from various sources including health care team, electronic records, market participants and government, and transforming all external inputs to formulated logical constraints; and passing the logical constraints through satisfiability modulo theory solver against the safely parameters or properties to determine whether the control mechanism is to be activated, wherein the wherein the activation of the control mechanism is based on two factor authentication or two factor validation.

According to exemplary embodiments, when the control mechanism is activated, the controlling module 332 may control dispensing amount of the first medication or the second medication.

According to exemplary embodiments, when the control mechanism is activated, the IHM 302a may monitor biometric data of a patient in real time; and interface with the patient's healthcare provider computing device and medication inventory computing device to administer the appropriate type and amount of medication to the patient that are appropriate given the patient's current health state in real time.

Further details will be provided below with respect to FIGS. 5-9.

Figure 5:
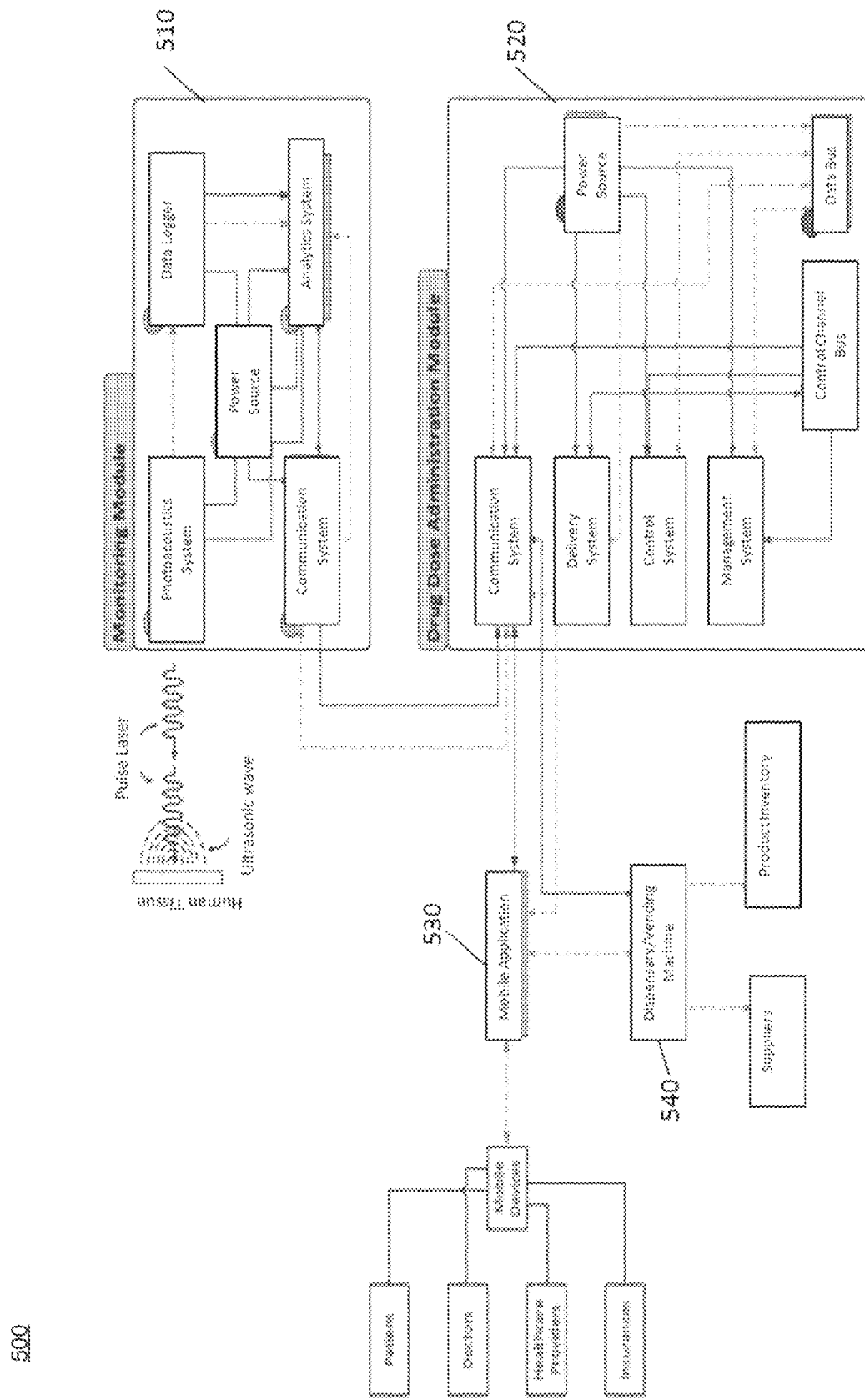
FIG. 5 illustrates a system for integrated healthcare management, according to an example embodiment.

FIG. 5 illustrates a system for integrated healthcare management, according to an example embodiment. In FIG. 5, in example embodiments, the system 500 includes a monitoring module 510, a drug administration module 520, a mobile application 530 and a medication dispensary 540. In example embodiments, the monitoring module 510 includes one or more devices configured to collect biometric data from a person or patient. For example, the monitoring module 510 may include a photo-acoustics system, a data logger, an analytics system, a power source and a communication system. For example, the monitoring module 510 may be a stand-alone device configured to be attached to, or worn by, a person being monitored. Accordingly, the monitoring module 510 may include an independent power source. The photo-acoustics system may be configured to, e.g., send a laser pulse to the human tissue of the person and to detect the returning acoustic wave from the human tissue. In example embodiments, the photo-acoustics system detects the wave signal and derives biometric data based on the detected wave signal returned from the human tissue. Specifically, the detected wave signal may be stored in a data logger and transmitted to an analytics system that derives the biometric data from the logged data provided by the acoustics system. In example embodiments, the IHM module 302, 302a illustrated in FIG. 3 transmits the biometric data outside of the monitoring module 510. For example, the IHM module 302, 302a transmits the biometric data to a central repository such as the patient health database 306(1)

illustrated in FIG. 3. The IHM module 302, 302a may also transmit biometric data to the drug administration module 520.

In example embodiments, the drug administration module 520 is configured to receive the biometric data from the monitoring module 510, and to also receive the type, amount and frequency of dispensation of the appropriate medication to the patient from the IHM module 302, 302a. For example, the drug administration module 520 may be a stand-alone device configured to be attached to the patient so as to allow for drug dispensation to the patient. For example, the drug administration module 520 may include an independent power source, a communication system configured to receive the biometric data provided from the monitoring module 510, the medication dispensation instructions from the IHM module 302, 302a, and a delivery system configured to deliver the medication. For example, the delivery system may include an injection device such as, e.g., a syringe, an array or syringes, or a micro-needle array, permanently or semi-permanently inserted into the body of the patient so as to facilitate the dispensation of the medication to the patient. The drug administration module 520 may also include a control system configured to control that the correct amount of medication is provided to the patient based on the instructions received from the IHM module 302, 302a, and a management system configured to manage the flow of data and of instructions from the communication system to the control system and the delivery system. In example embodiments, the drug administration module 520 may also include a data bus and a control channel bus to ensure the integrity of the data flowing between the various systems of the drug administration module 520, as well as between the IHM module 302, 302a and the drug administration module 520.

In example embodiments, the IHM module 302, 302a may control the drug administration module 520 via, e.g., a mobile application 530 functionally coupled to a central database or to a plurality of databases such as databases 306(1)-306(3) described in FIG. 3, each of the databases including information related to the patient such as the patient's medical condition and updated medical records, the patient's doctor, the patient's healthcare provider, the patient's health insurance and the like. Accordingly, the IHM module 302, 302a controls the mobile application 530 as an interface between the drug administration module 520 and the databases 306(1)-306(3), the mobile application 530 providing instructions to the drug administration module 520 for administering the medication to the patient, the frequency of dispensation of the medication and the doses of the medication to be administered to the patient, based on instructions received from the IHM module 302, 302a, which are based on the data received from the monitoring module 510. In example embodiments, the IHM module 302, 302a also controls the mobile application 530 to manage the medication or medical equipment inventory as well as communication with suppliers, and to manage a dispensary 540 of medicine or medical equipment, the dispensary 540 being located, e.g., close to the location of the patient.

Accordingly, the system 500 for integrated healthcare management, according to an example embodiment, allows for the remote monitoring of a person's current biometric data collected by the monitoring module 510 in real time and, based on the patient's up-to-date medical condition stored a database and based on the patient's current biometric data, determines and dispenses appropriate drugs in appropriate amounts, i.e., the drugs and the amounts of the drugs that are medically recommended to address the patient's current medical condition, to the patient via the drug administration module 520.

Figure 6:
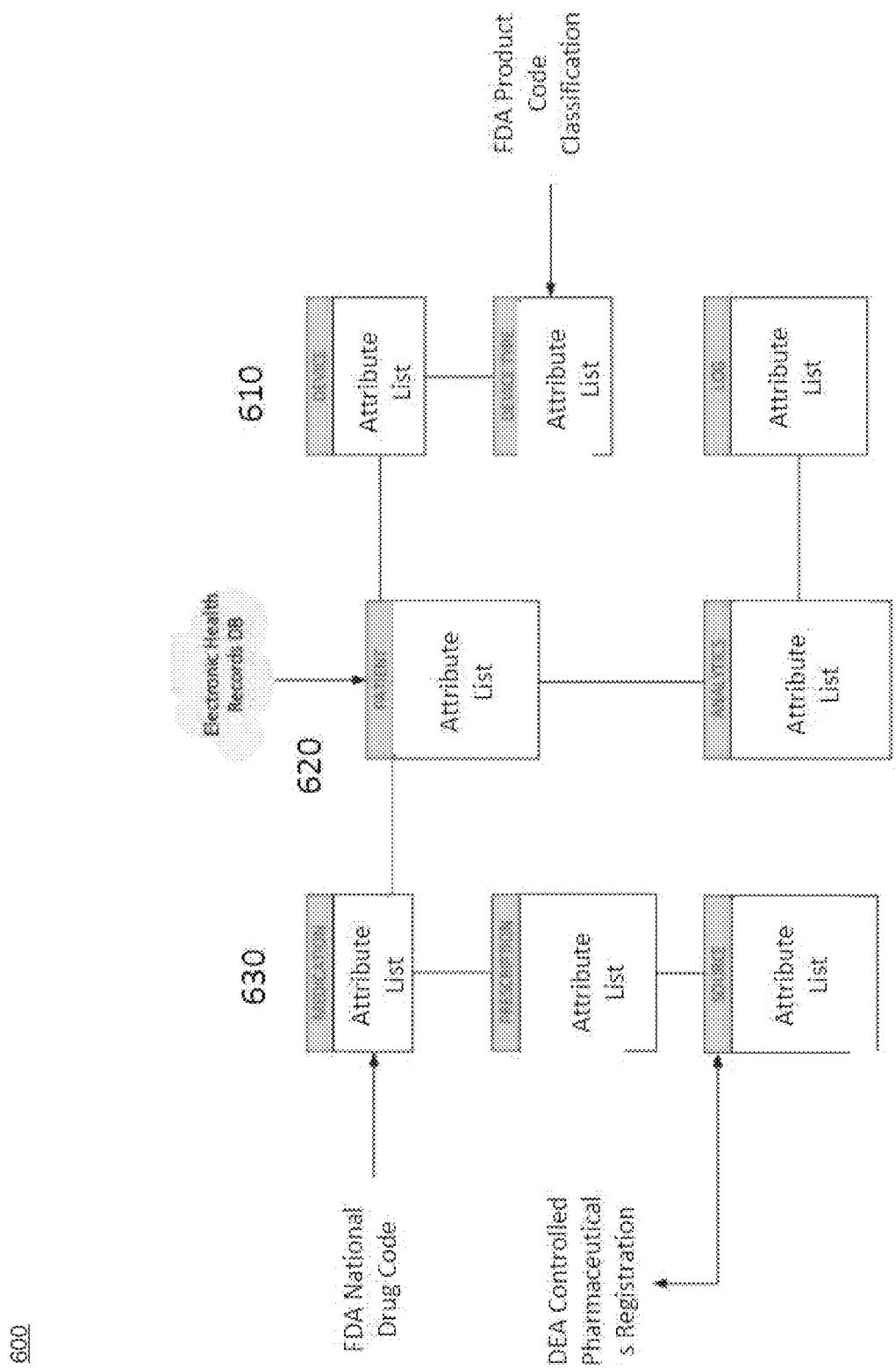
FIG. 6 illustrates a system for integrated healthcare management, according to an example embodiment.
Figure 7A:
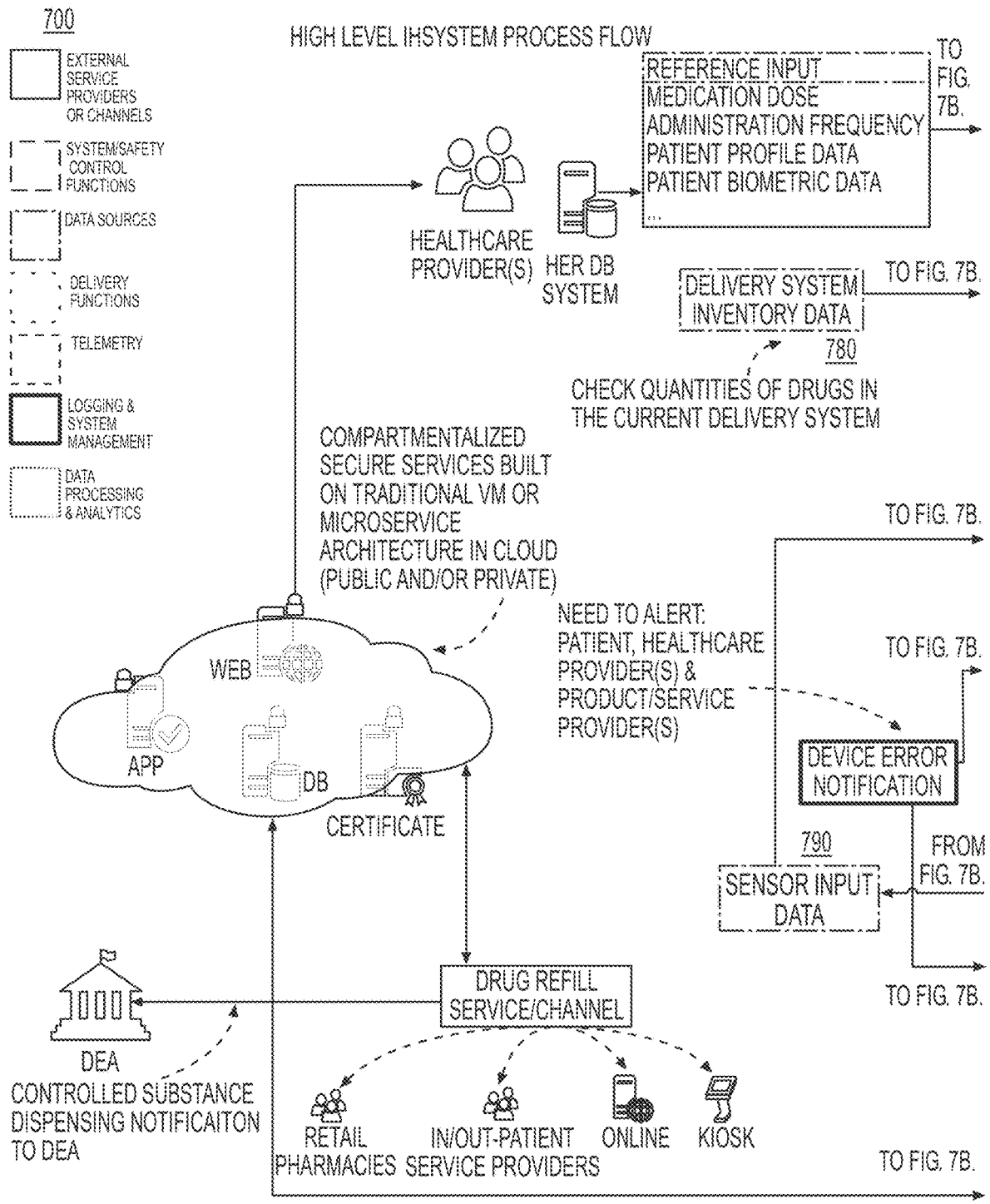
FIGS. 7A, 7B, 7C, and 7D illustrate a process flow for integrated healthcare management, according to an example embodiment.
Figure 7B:
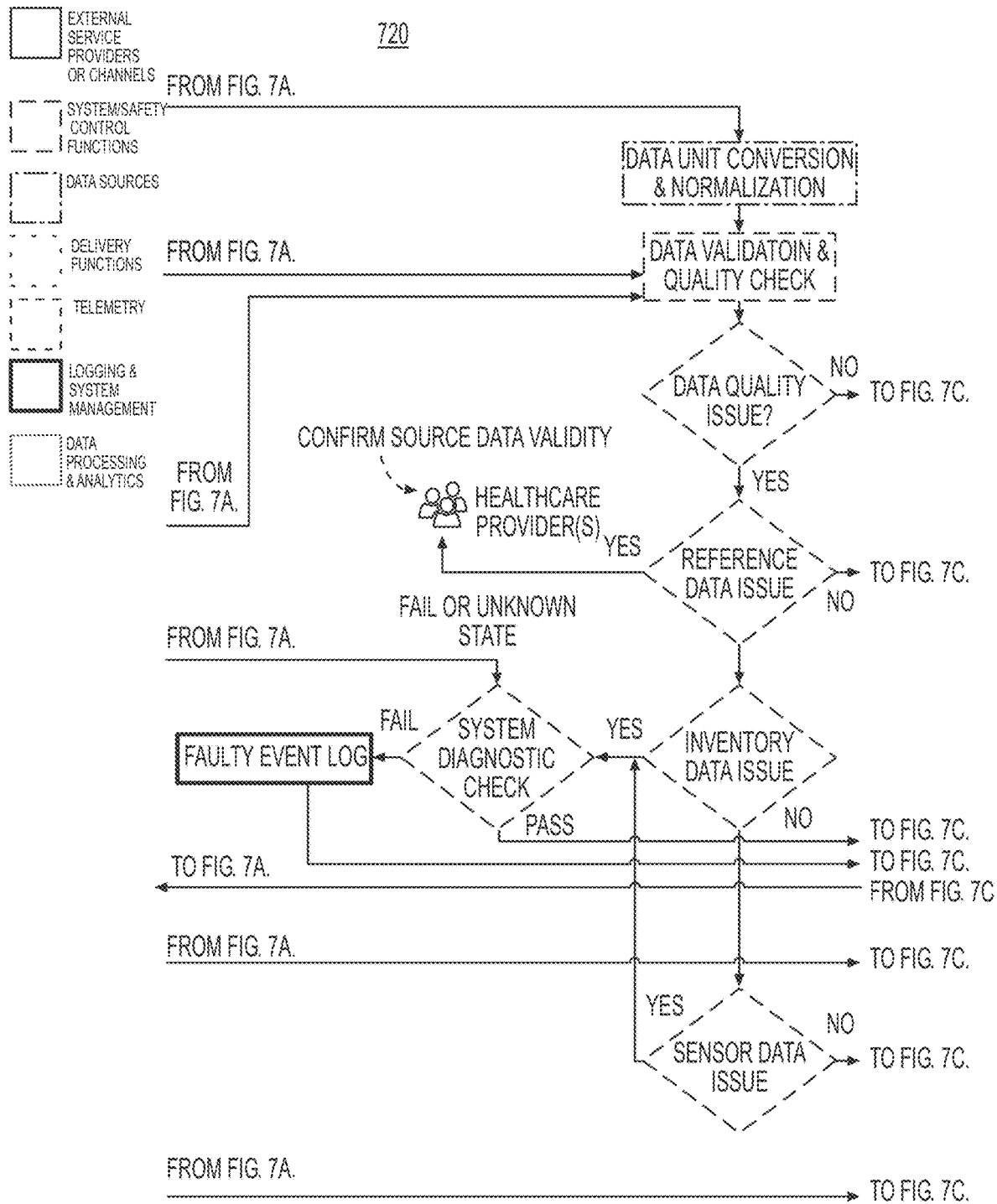
Figure 7C:
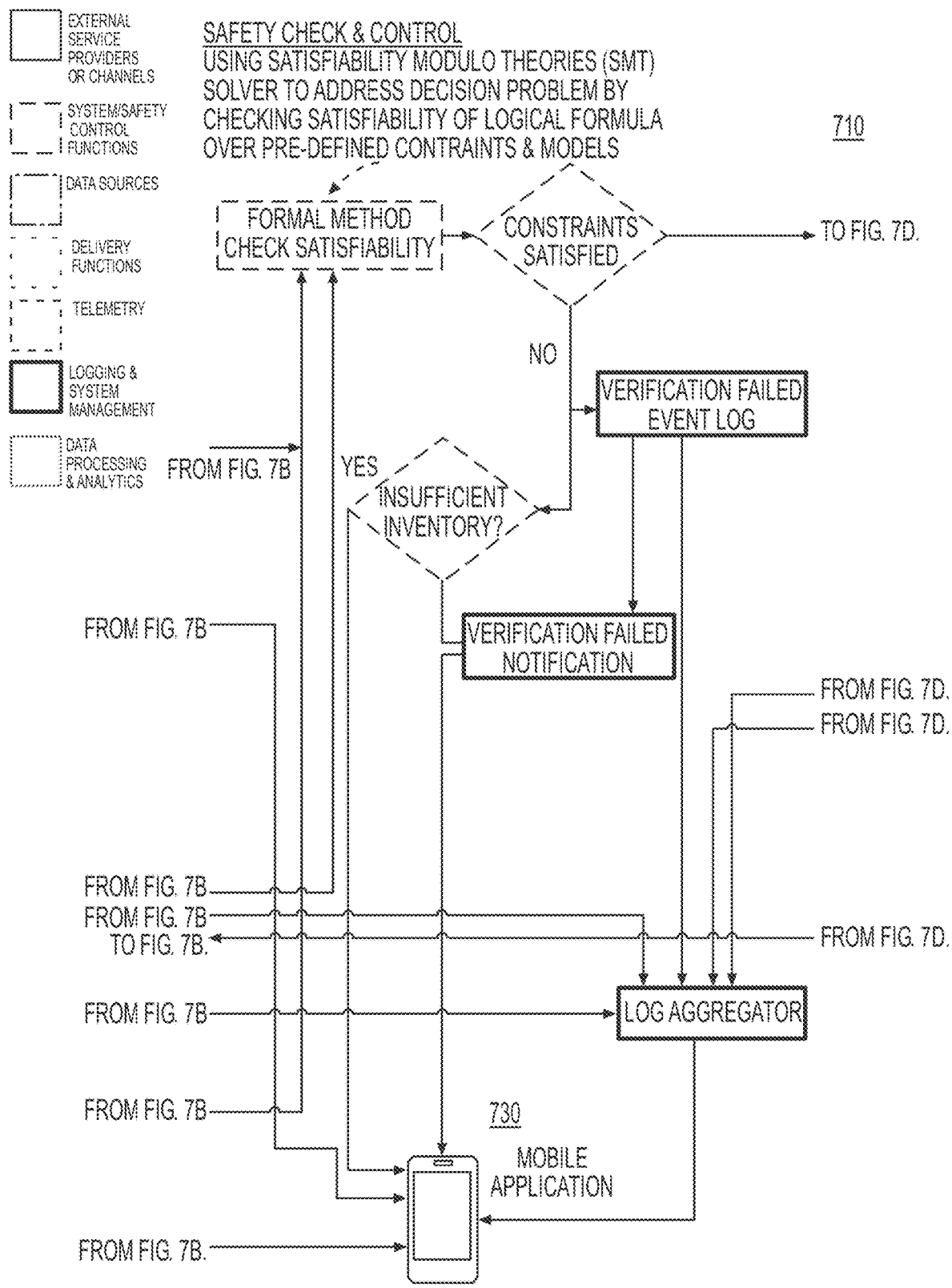
Figure 7D:
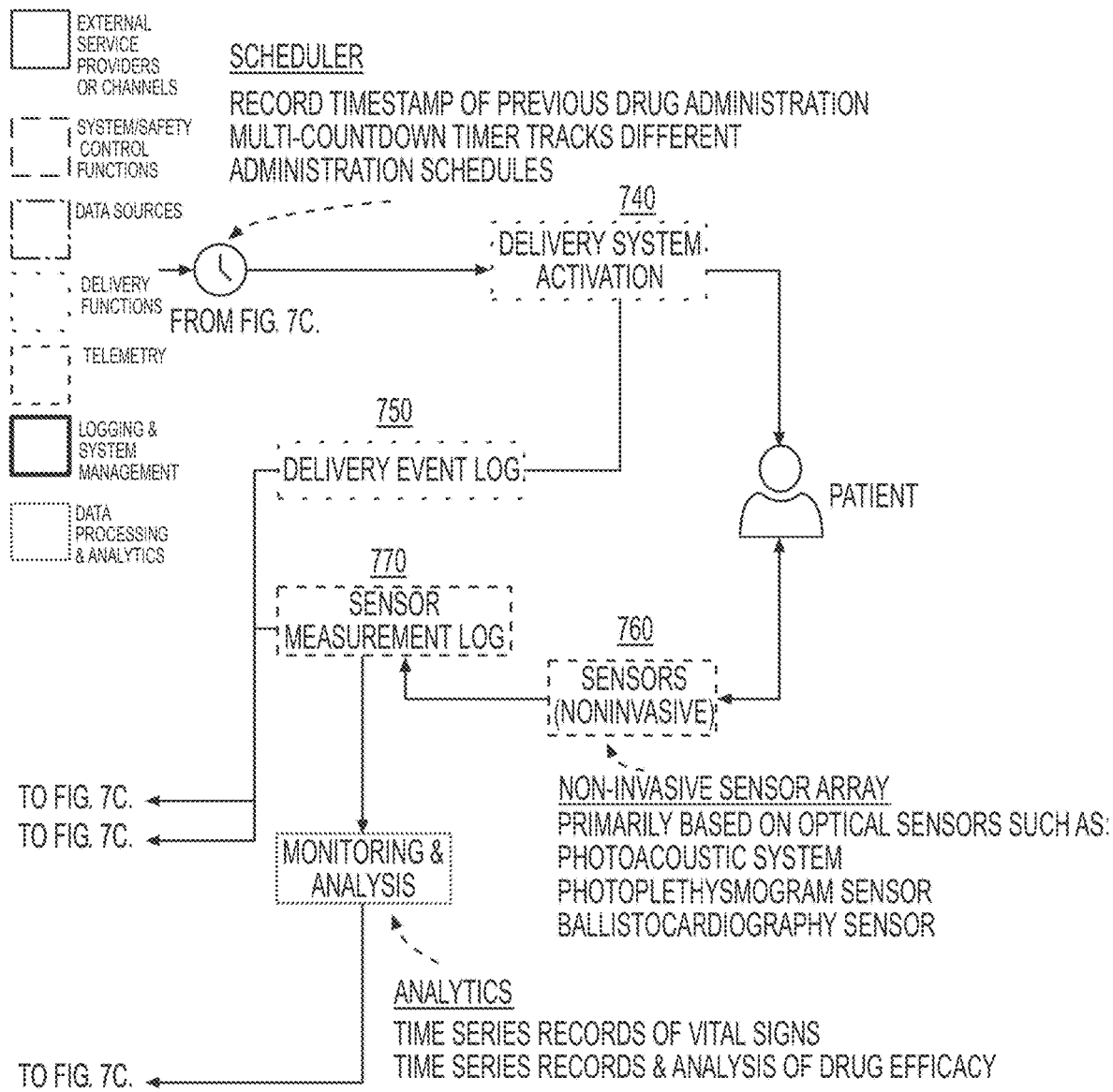

FIG. 6 illustrates system attributes for integrated healthcare management, according to an example embodiment. In example embodiments, the system includes three (3) modules: a device module 610, similar to the drug administration module 520 and configured to administer drugs to a patient, and/or similar to the monitoring module 510 configured to monitor the patient's biometric data, a patient module 620, similar to the IHM module 302, 302a and the patient health database 306(1) and configured to recognize a given patient and manage the types and amounts of medication to be administered to the recognized patient, if needed, based on the patient's biometric data and based on electronic health records (EHR) from the patient's healthcare provider, and a resources module 630 similar to the IHM module 302, 302a and the databases 306(2) and 306(3) and configured to store and update medication information for the patient, prescriptions provided by the medical provider, relevant Food and Drug Administration (FDA) regulations and codes with respect to the medication to be administered to the patient, relevant Drug Enforcement Agency (DEA) information relative to controlled substances and prohibitions, and the like. Accordingly, the system illustrated in FIG. 6 includes a framework summarizing the functional requirements of interoperation within the system of the example embodiments and external data sources and models such as electronic health records (EHR) from various healthcare providers and government regulatory agencies. In example embodiments, the system illustrated in FIG. 6 is flexible and may not prescribe or rely on any specific physical data modeling techniques.

FIGS. 7A, 7B, 7C, and 7D illustrate illustrates a process flow for integrated healthcare management, according to an example embodiment. In FIG. 7, in example embodiments, the process flow includes three (3) poles, a Patient Pole 710, a Healthcare Provider Pole 720 and a mobile application 730 configured to be an interface between the Patient Pole 710 and the Healthcare Provider Pole 720. The term "pole" is used herein to designate a location or combination of locations and devices configured to achieve a same function. The Patient Pole 710 includes a Delivery System Activation module 740 where the IHM module 302, 302a discussed in FIG. 3 controls the drug administration module 520 discussed in FIG. 5 to administer drugs to the patient, and a Delivery Event Log module 750 configured to record the delivery of the drug to the patient. The Patient Pole 710 also includes a Sensors module 770, configured to control the biometric sensor, and a Sensor Measurement Log module 760 configured to record the measurements performed by the Sensors module 770. In example embodiments, the IHM module 302, 302a transmits the recorded drug deliveries and sensor measurements to a mobile application 730, which is an interface between the Patient Pole 710 and the Healthcare Provider Pole 720. In example embodiments, the Healthcare Provider Pole 720 includes a Delivery System Inventory module 780 configured to manage the delivery of drugs to the patient based on the information provided from the Patient Pole 710 via the mobile application 730, and an Inventory module 790 configured to manage the inventory of drugs available to the patient and to manage the supply and shelf life of the drugs to be delivered to the patient. In example embodiments, the IHM module 302, 302a performs data validation and quality check of the integrity of the data being transmitted between the Patient Pole 710 and the Healthcare Provider Pole 720.

Figure 8:
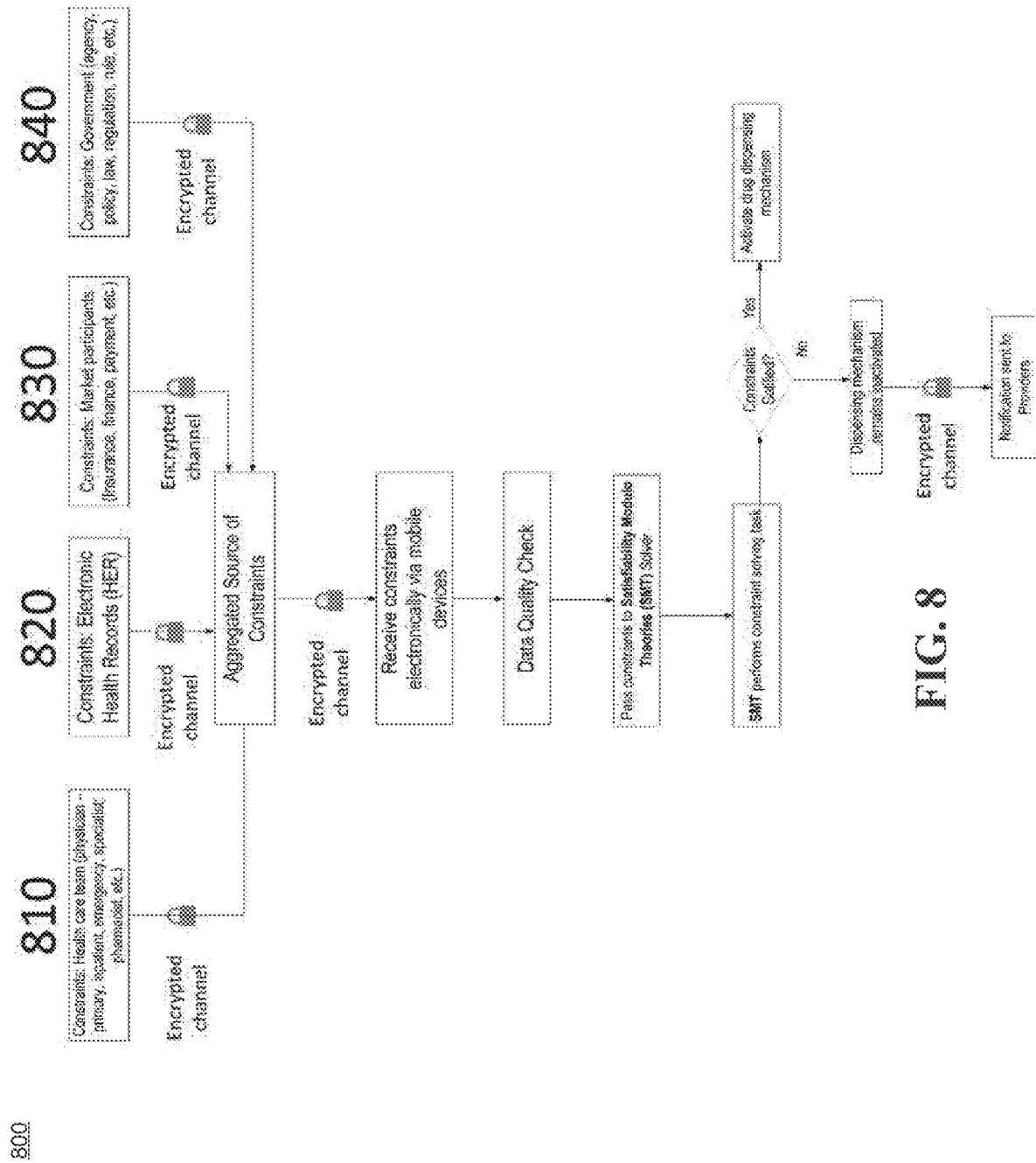
FIG. 8 illustrates a safety control process during a process of integrated healthcare management, according to an example embodiment.

FIG. 8 illustrates a safety control process during a process of integrated healthcare management, according to an example embodiment. In FIG. 8, the IHM module 302, 302a takes a number of constraints into account, such as personnel constraints 810, management constraints 820, market participant constraints 830 and regulatory constraints 840. The personnel constraints 810 include the healthcare team involved in the treatment of a patient such as the primary care physician(s), the emergency physician, the pharmacist, and the like. The management constraints 820 relate to management of electronic health records including security, integrity and availability of the records. The market participant constraints 830 include the health insurance company, any third-party payment company, and the like. The regulatory constraints 840 include medicine safety rules, regulations, laws and policies imposed by governmental agencies. In example embodiments, the IHM module 302, 302a aggregates the constraints 810, 820, 830 and 840 and solves the constraints via a solver such as, e.g., a satisfiability modulo theories (SMT) solver, which is an algorithm based on a generalized Boolean methodology. Specifically, the IHM module 302, 302a solves the determination of the type and amount of drug to be delivered to the patient based on the patient's sensed biometric data and based on the available drug data from the inventory data.

Figure 9:
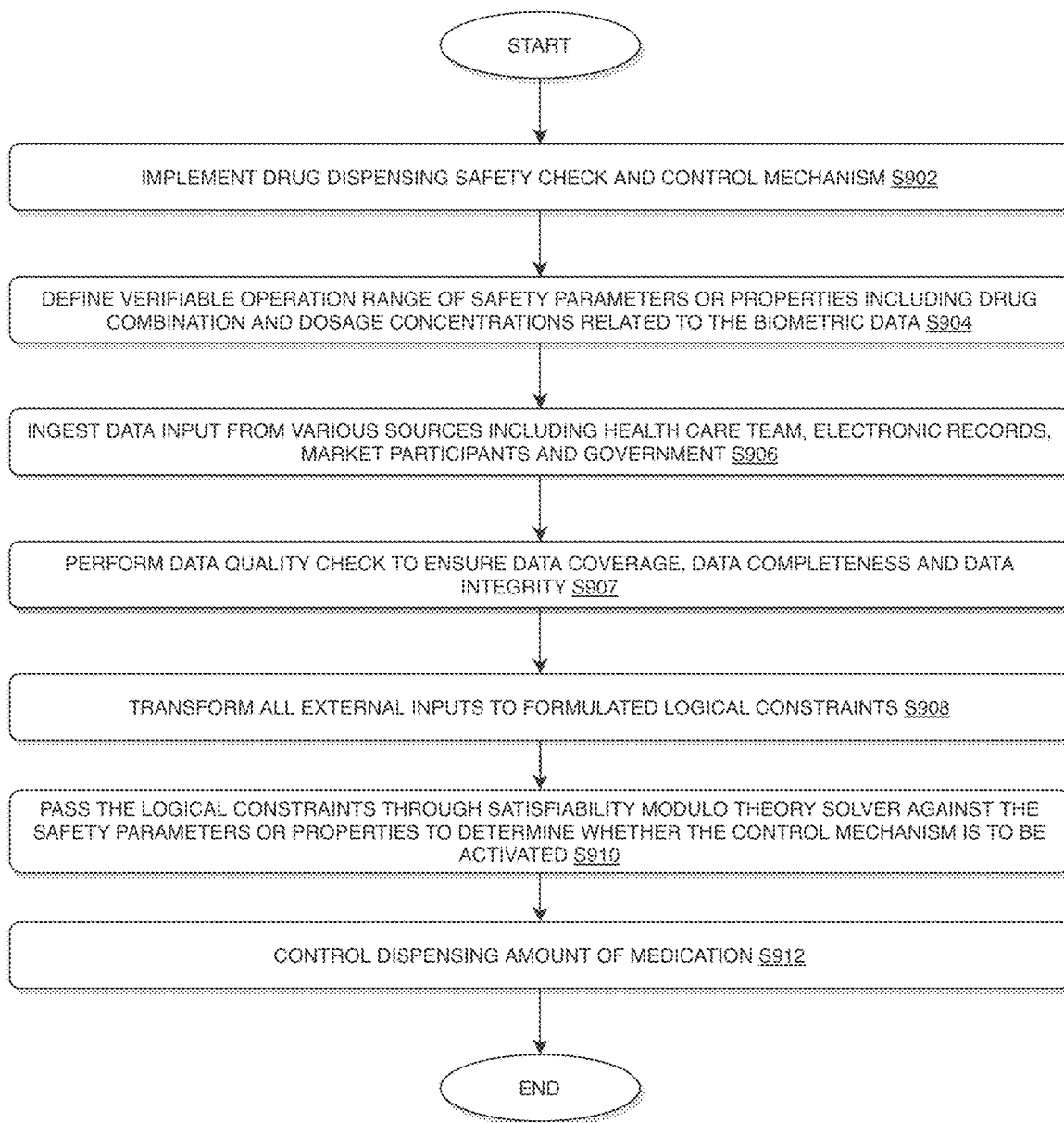
FIG. 9 illustrates a flow diagram of implementing a drug dispensing safety check and control mechanism, according to an example embodiment.

FIG. 9 illustrates a flow diagram of implementing a drug dispensing safety check and control mechanism, according to an example embodiment.

In the process 900 of FIG. 9, at step S902, drug dispensing safety check and control mechanism may be implemented. At step S904, verifiable operation range of safety parameters or properties may be defined including drug combination and dosage concentrations related to the biometric data. At step S906, data input may be ingested from various sources including health care team, electronic records, market participants and government. At step S907, all inputs need to go through quality check to ensure data coverage, completeness, consistency, accuracy and integrity before moving to input constraints creation stage S908. At step S908 all external inputs may be transformed to formulated logical constraints. At step S910, the logical constraints may be passed through satisfiability modulo theory solver against the safely parameters or properties to determine whether the control mechanism is to be activated. According to exemplary embodiments, the activation of the control mechanism may be based on two factor authentication or two factor validation. One of ordinary skill in the art would readily understand such two factor authentication or two fact validation processes.

At step S912, dispensing amount of medication may be controlled. For example, when the control mechanism is activated, the process 900 may be further include controlling dispensing amount of the first medication or the second medication disclosed above with reference to FIGS. 3-8.

According to exemplary embodiments, when the control mechanism is activated, the process 900 may be further include: monitoring biometric data of a patient in real time; and interfacing with the patient's healthcare provider computing device and medication inventory computing device to administer the appropriate type and amount of medication to the patient that are appropriate given the patient's current health state in real time as disclosed above with respect to FIGS. 3-8.

According to exemplary embodiments, a non-transitory computer readable medium may be configured to store instructions for integrated healthcare management implemented by a processor on a sensor-equipped computing device. According to exemplary embodiments, the instructions, when executed, may cause a processor embedded within the IHM module 302 or 302a to perform the following: generating a medical record data, accessing information about a first treatment related to the medical record data; obtaining, by the sensor and validated by the processor, biometric data related to the first treatment; processing the biometric data; determining whether the first treatment is appropriate with respect to the biometric data; in response to the first treatment being appropriate with respect to the biometric data, outputting first information related to a first administration of a first medication; and in response to the first treatment not being appropriate with respect to the biometric data determining a second treatment; and outputting second information related to a second administration of a second medication based on the determined second treatment. The processor may be the same or similar to the processor 104 as illustrated in FIG. 1 or the processor embedded within the IHM device 202, IHM device 301, and the IHM module 302, 302a.

According to exemplary embodiments, the instructions, when executed, may further cause the processor 104 to perform the following: receiving real-time feedback data corresponding to an efficacy of the first medication; determining a modified dosage level of the first medication based on the received real-time feedback data; and modifying the first information related to the first administration of the first medication based on the determined modified dosage level of the first medication.

According to exemplary embodiments, the instructions, when executed, may further cause the processor 104 to perform the following: receiving real-time feedback data corresponding to an efficacy of the second medication; determining a modified dosage level of the second medication based on the received real-time feedback data; and modifying the second information related to the second administration of the second medication based on the determined modified dosage level of the second medication.

Accordingly, with this technology, it is possible to monitor biometric data of a patient in real time and interface with the patient's healthcare provider and medication inventory to administer the appropriate type and amount of medication to the patient that are appropriate given the patient's current health state in real time. The following examples provide illustrations of the above advantages.

In example embodiments, when a doctor prescribes medicine for a patient, the prescription is uploaded to the IHM system 100 illustrated in FIG. 1. With reference to FIGS. 3 and 3A, the IHM module 302, 302a updates the patient's account at databases 306(1)-306(3) with prescription and health details which can be accessed via, e.g., the patient's mobile and online accounts at devices 308(1) and 308(1). In example embodiments, the prescription becomes available for filling at any one of a number of providers within the patient's healthcare network. The patient visits an in-network provider and is able to obtain prescription from a vending device after securely authenticating their identity. As the prescription is dispensed to the patient, the IHM module 302, 302a updates the patient health database 306 (1), the medication database 306(2) and the treatment database 306(3) to indicate that prescription vending has occurred, the IHM module 302, 302a updates the patient insurance information, and the patient account now reflects the vended prescription. In example embodiments, the IHM module 302, 302a controls a drug dispensing device 312 configured to dispense a given type and dosage of drugs to a patient. In example embodiments, the drug dispensing device may include one or more storage chambers configured to store one or more drug(s) in liquid form; a dispensing mechanism with physical connections to the drug chambers, an interface module configured to communicate with the IHM device 301; a drug refilling or disposal mechanism; and an independent power source such as, e.g., a portable battery.

In example embodiments, when a prescription scheduled time for a drug dosage application is reached, a mobile device at, e.g., the mobile application 530 illustrated in FIG. 5, confirms the scheduled time and dosage and sends a secure, encrypted message to the drug dose administration module 520 to dispense the required dosage. When the required dosage is administered to the patient, the IHM module 302, 302a updates the dosing schedule at, e.g., the treatment database 306(3), the healthcare provider records, and the patient's medical records at databases 306(2) and 306(3).

In example embodiments, the IHM module 302, 302a, via the monitoring module 510 illustrated in FIG. 5, monitors the patient's vital and biometric signals and prescription impact based upon predefined patterns of prescription detection and expected resulting biological reactions. The IHM module 302, 302a transmits an updated status of the patient to the patient health database 306(1), the medication database 306(1) and the treatment database 306(3).

In example embodiments, when the IHM module 302, 302a, via the monitoring module 510 illustrated in FIG. 5, monitors the patient's vital and biometric signals, the IHM module 302, 302a compares the monitored signals to known biological patterns. The IHM module 302, 302a observes and confirms identified patterns through several measurement iterations. Accordingly, pattern matching may trigger an alert if the monitored signals correspond to a patient of disease or another medical emergency.

In example embodiments, when the IHM module 302, 302a, via the monitoring module 510 illustrated in FIG. 5, triggers an alert during patient monitoring, the IHM module 302, 302a triages the alert based upon existing patterns, current patient prescriptions and patient information. If the alert involves a known condition for which the treating medication exists in the patient's treatment database 306(3), the IHM module 302, 302a controls the dispensation of the medication, at the required dosage that is defined in the treatment database 306(3), to the patient. When the drug is dispensed, the IHM module 302, 302a updates the patient records at the patient health database 306(1), the medication database 306(1) and the treatment database 306(3).

In example embodiments, when the IHM module 302, 302a, via the monitoring module 510 illustrated in FIG. 5, triggers an alert during patient monitoring, the IHM module 302, 302a triages the alert based upon a known pattern that is new with respect to the patient, i.e., the known pattern has not been previously detected for that particular patient. Specifically, the patient did not previously exhibit this newly discovered pattern. The IHM module 302, 302a triages the alert based upon existing patterns, prescriptions and patient information. If the IHM module 302, 302a determines that the severity of the alert is routine and not urgent or critical, the IHM module 302, 302a notifies the healthcare provider. In example embodiments, the IHM module 302, 302a schedules an appointment, submits the prescription to the healthcare provider and alerts the patient to fill a prescription.

In example embodiments, when the IHM module 302, 302a, via the monitoring module 510 illustrated in FIG. 5, triggers an alert during patient monitoring, the IHM module 302, 302a triages the alert based upon a known pattern that is new with respect to the patient, i.e., the known pattern has not been previously detected for that particular patient. Specifically, the patient did not previously exhibit this newly discovered pattern. The IHM module 302, 302a triages the alert based upon existing patterns, prescriptions and patient information. If the IHM module 302, 302a determines that the severity of the alert is critical, the IHM module 302, 302a dispatches emergency services and provides patient details while the emergency services are on the way to reaching the patient. In example embodiments, the IHM module 302, 302a also notifies the healthcare provider and other relevant third parties.

In example embodiments, when the IHM module 302, 302a, via the monitoring module 510 illustrated in FIG. 5, triggers an alert during patient monitoring, the IHM module 302, 302a triages the alert based upon a known pattern that is new with respect to the patient. Specifically, the patient did not previously exhibit this newly discovered pattern. The IHM module 302, 302a triages the alert based upon existing patterns, prescriptions and patient information. If the IHM module 302, 302a determines that the severity of the alert can be mitigated by patient action, then the IHM module 302, 302a alerts the patient with specific instructions and/or action items, and notifies the healthcare provider and other relevant third parties.

In example embodiments, when the IHM module 302, 302a, via the monitoring module 510 illustrated in FIG. 5, triggers an alert during patient monitoring, the IHM module 302, 302a triages the alert based upon a known pattern and one for which the patient has a prescription but has no remaining doses available in inventory. In example embodiments, the IHM module 302, 302a directs the patient to the closest in-network dispensary to obtain a prescription if remaining refills are available on the patient account that is stored at the patient health database 306(1) and retrieved by the IHM module 302, 302a. If no additional refills are credited, the IHM module 302, 302a notifies the healthcare provider and other nearby in-network providers with an emergency request for the needed prescription. The patient can then obtain the medication at a local dispensary after authentication through the mobile application 530 illustrated in FIG. 5, and the IHM module 302, 302a notifies the healthcare provider as well as any relevant third parties.

In example embodiments, when the IHM module 302, 302a, via the monitoring module 510 illustrated in FIG. 5, monitors the patient's biometric data, and the data indicates an outbreak of known medical condition patterns such as, e.g., flu, measles, cholera, and the like. The IHM module 302, 302a displays the outbreak on a map at, e.g., the computer display 108 illustrated in FIG. 1, reviews inventories of necessary medicine at databases 306(2) and 306(3), and requests increases of on-hand inventory at dispensaries such as, e.g., the dispensary 540 illustrated in FIG. 5. The IHM module 302, 302a notifies the patient, as well as other patients, of the identified pattern, and provides directions to the patients on necessary steps to be taken in order to prevent the spread of the outbreak. In example embodiments, the IHM module 302, 302a credits drug prescriptions, and directs the patients to the closest dispensary, such as the dispensary 540 illustrated in FIG. 5. If the IHM module 302, 302a, via the monitoring module 510, detects that the outbreak is severe, the IHM module 302, 302a provides additional emergency alerts to, e.g., media, health care providers, public transportation, and/or any other relevant third parties.

In example embodiments, if the patient is experiencing increased anxiety, pain or other condition that is not easily measured by standard biological indicators, the patient requests, via a mobile application 530 at a mobile device, a one-time dosage, or an increase in the regular dosage for all future dosages. If the request for the increase in the dosage is a one-time request, the IHM module 302, 302a notifies the healthcare provider, and controls the dispensation of the medication at the requested increased dosage via the drug dose administration module 520. If the request for the increased dosage is repeated beyond a desired or predefined threshold, or if the request is a request to permanently increase the dosage of medication, the IHM module notifies the healthcare provider, and only dispenses the increased dosage if approved by the healthcare provider. If the increased dosage is approved, the IHM module 302, 302a controls the dispensing of the increase dosage via the drug dose administration module 520. In example embodiments, upon receiving a request for an increased dosage, whether temporary or permanent, the IHM module 302, 302a may trigger an automatic prescription review and discussion with the patient's healthcare provider.

In example embodiments, if a patient seeks advice from a healthcare provider, the IHM module 302, 302a transmits the request via a mobile application at a mobile device, such as mobile application 530 illustrated in FIG. 5. The IHM module 302, 302a alerts the healthcare provider, and the patient is given an estimation of the provider's availability. In example embodiments, the healthcare provider is able to communicate with the patient via, e.g., a two-way voice or video chat over the mobile device.

In example embodiments, the IHM module 302, 302a may detect that a number of patients are in close proximity of each other patients, e.g., while commuting to work, based on the data provided by the GPS units contained within their mobile devices, the patients being within a given distance of a dispensing unit. If one of the patients is contagious, then all the remaining patients that are in close proximity to the contagious patient are notified of the possible exposure. The IHM module 302, 302a increases the monitoring specifically based on the contagion pattern, and at the first sign that any one of the patients exhibits symptoms of the contagion, the patient is prescribed appropriate medicine. In example embodiments, the IHM module 302, 302a monitors the contagion symptoms via the monitoring module 510 illustrated in FIG. 5. In example embodiments, the IHM module 302, 302a does not provide personal identifiable information of a contagious patient to other patients.

In example embodiments, emergency personnel may be called or dispatched to an in-network patient via, e.g., a notification from a healthcare provider, from the patient or from another interested third party. As a result, the IHM module 302, 302a may increase the monitoring of the patient in order to reduce delays in biometric measurements and determine whether any measurements reach or exceed predefined limits, which may be indicative of an acute emergency. The information received via the monitoring of the patient by the IHM module 302, 302a may include relevant details about the patient such as, e.g., biological measurements taken during the previous hour as recorded by the monitoring module 510, as illustrated in FIG. 5. The IHM module 302, 302a also receives details about all medicine dispensed through the drug administration module 520, including the time of dispensation and the amount of drug dosage. In example embodiments, the IHM module 302, 302a transmits this information in a streaming manner in real time to the emergence personnel until the engagement of the emergency personnel with the patient is concluded. If the patient is transferred to a hospital or other healthcare facility, the IHM module 302, 302a transmits the information to, e.g., the interested third party for the duration of patient care. The IHM module 302, 302a also transmits the information to the healthcare provider.

In example embodiments, in the case military units being dispatched in combat zones, the drug administration module 520 for all military personnel may include a predefined battlefield dispensing packet, which may be used as an additional dispensing unit that can be uses in case of injury or other situation requiring medication. In example embodiments, the dispensing packet may include emergency medication as well as performance enhancing supplements, and the IHM module 302, 302a may control the automatic administration of medication to the soldiers in order to combat the effects of illness, injury, chemical warfare, allergic reactions, fatigue, malnutrition, chemical imbalances, and the like. A monitoring module 510 may also monitor various health readings that the IHM module 302, 302a can transmit to the command center in order to monitor the wellbeing of each solider on the field.

In example embodiments, people traveling to high risk areas can be given a drug administration module 520 that includes drugs that are specific to addressing common diseases in the high risk travel area.

In example embodiments, people traveling on cruise ships and airlines can be prescribed motion sickness, anxiety medications or other drugs for use while on vacation or traveling. For example, these drugs may be limited in quantity and tailed to the specific trip.

In example embodiments, the drug administration module 520 may include vaccines that can be dispensed automatically, or the vaccines may be stocked at one or more dispensers at, e.g., an employment site. In example embodiments, patients may request the vaccine to be prescribed and dispensed to them via their mobile device 530, and the vaccines may be dispensed via the drug administration module 520 after the IHM module 302, 302a monitors the health and prescription data of the given patient and determines that vaccination at that time is appropriate.

In example embodiments, the IHM module 302, 302a monitors pregnancies and allows for remote monitoring of a mother and her baby via the monitoring module 510. The IHM module 302, 302a monitors the health of the mother and/or her baby in real time by comparing preset patterns with biometric data collected via the monitoring module 510, and may trigger a predefined series of events including, e.g., transportation to the hospital and notification of the delivery healthcare provider while the expecting mother is on her way to the hospital. The IHM module 302, 302a may continue to monitor the biometric data of the mother and transmit the data to the delivery facility and personal in real time.

In example embodiments, elderly care units are provided dashboard to monitor all patients' data from a central desk, where the IHM module 302, 302a triggers triggering patient interaction, medication release or other necessary medical attention based on predefined alerts detected via the monitoring module 510.

In example embodiments, the IHM module 302, 302a remotely monitors isolated patients with better or increased frequency via two-way voice/video capabilities if the IHM module 302, 302a detects a triggering or predefined pattern.

In example embodiments, in the case of catastrophic events such as accidents, car crashes, construction accident, and the like, where the vital statistics of a victim likely undergoes demonstrably life threatening changes, the IHM module 302, 302a triggers immediate emergency responder notifications with, e.g., location identification and provides all available relevant information to the parties concerned such as, e.g., emergency responders or local law enforcement.

In example embodiments, in cases of addiction and rehabilitation, for a person suffering with addiction, the IHM module 302, 302a may automatically control the dispensation of medication via the drug administration module 520 to combat, e.g., symptoms of withdrawal, and/or to dispense medications that deter the use of specific substances. In example embodiments, the monitoring module 510 may monitor, e.g., various forms of tamper resistance in the patient, as well as the presence of specific chemicals.

In example embodiments, in the case of athletes, professional or amateur, the monitoring module 510 may include an array of sensors configured to take biometric measurements related to sport medicine. For example, the monitoring module 510 may measure various parameters such as, e.g., blood oxygenation, blood pressure, hydration, muscle fatigue, detection of harmful substances, and any other performance measurements. The measured data may be used, e.g., to design workouts and nutritional regimens unique to the physiology of the individual athlete.

In example embodiments, in a fully manual mode, a user of the drug administration module 520 may manually administer the medication to themselves in the event of, e.g., a systems or power failure. Furthermore, the drug administration module 520 may be provided with a tamper resistant mechanism by including controls that facilitate the intentional (or automatic) release of medication, but prevents the accidental or malicious release of the same medication. In example embodiments, the IHM module 302, 302a may only monitor the biometric data of a patient via the monitoring module 510, collects the biometric data and provides communication/alerting mechanisms as necessary, but does not administer medication via a drug administration module.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the present disclosure in its aspects. Although the invention has been described with reference to particular processes, materials and embodiments, the invention is not intended to be limited to the particulars disclosed; rather the invention extends to all functionally equivalent structures, methods, and uses such as are within the scope of the appended claims.

For example, while the computer-readable medium may be described as a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the embodiments disclosed herein.

The computer-readable medium may comprise a non-transitory computer-readable medium or media and/or comprise a transitory computer-readable medium or media. In a particular non-limiting, exemplary embodiment, the computer-readable medium can include a solid-state memory such as a memory card or other package that houses one or more non-volatile read-only memories. Further, the computer-readable medium can be a random-access memory (RAM) or other volatile re-writable memory. Additionally, the computer-readable medium can include a magneto-optical or optical medium, such as a disk or tapes or other storage device to capture carrier wave signals such as a signal communicated over a transmission medium. Accordingly, the disclosure is considered to include any computer-readable medium or other equivalents and successor media, in which data or instructions may be stored.

Although the present application describes specific embodiments which may be implemented as computer programs or code segments in computer-readable media, it is to be understood that dedicated hardware implementations, such as application specific integrated circuits, programmable logic arrays and other hardware devices, can be constructed to implement one or more of the embodiments described herein. Applications that may include the various embodiments set forth herein may broadly include a variety of electronic and computer systems. Accordingly, the present application may encompass software, firmware, and hardware implementations, or combinations thereof. Nothing in the present application should be interpreted as being implemented or implementable solely with software and not hardware.

Although the present specification describes components and functions that may be implemented in example embodiments with reference to particular standards and protocols, the disclosure is not limited to such standards and protocols. Such standards are periodically superseded by faster or more efficient equivalents having essentially the same functions. Accordingly, replacement standards and protocols having the same or similar functions are considered equivalents thereof.

The illustrations of the embodiments described herein are intended to provide a general understanding of the various embodiments. The illustrations are not intended to serve as a complete description of the entirety of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for integrated healthcare management, the method being implemented by a processor on a sensor-equipped computing device, the method comprising:
generating, by the processor, a medical record data of a patient;
accessing, by the processor, information about a first treatment related to the medical record data of the patient;
transmitting, by an optical sensing device, a laser pulse towards human tissue of the patient, the sensor including a photo-acoustics system;
obtaining, by the optical sensing device and in real-time, acoustic ultra sonic wave returned by the human tissue;
collecting, via a wearable device attached to the patient and in real-time, each of a blood pressure, heartbeat rhythm and glucose levels;
deriving, by the processor, biometric data related to the first treatment based on the acoustic wave returned by the human tissue and each of the blood pressure, heartbeat rhythm and glucose levels;
processing, by the processor, the biometric data;
determining, by the processor, whether the first treatment is appropriate with respect to the biometric data;
in response to the first treatment being appropriate with respect to the biometric data, outputting first information related to a first administration of a first medication;
in response to the first treatment not being appropriate with respect to the biometric data:
modifying, by the processor and in real-time, a treatment recommendations for the patient and generating a second treatment to correspond to the derived biometric data, wherein the second treatment specifies a type, amount of dosage and frequency of dispensation of a second medication;
outputting second information related to a second administration of the second medication based on the determined second treatment;
providing, wirelessly to an administration module in a mobile terminal separate from the sensor-equipped computing device, instructions to administer the second treatment;
remotely performing an automated injection, by a medication dispensing device having a syringe and coupled to the mobile terminal, wherein the automated injection includes automatically and intravenously administering the second medication to the patient via the syringe inserted into the patient in response to the acoustic wave returned by the human tissue obtained by the optical sensing device and each of the blood pressure, heartbeat rhythm and glucose levels collected by the wearable device; and
after the second medication is administered to the patient, updating the medical record for the administrating of the second medication.

2. The method according to claim 1, further comprising:
receiving real-time feedback data corresponding to an efficacy of the first medication;
determining a modified dosage level of the first medication based on the received real-time feedback data; and
modifying the first information related to the first administration of the first medication based on the determined modified dosage level of the first medication.

3. The method according to claim 1, further comprising:
receiving real-time feedback data corresponding to an efficacy of the second medication;
determining a modified dosage level of the second medication based on the received real-time feedback data; and
modifying the second information related to the second administration of the second medication based on the determined modified dosage level of the second medication.

4. The method according to claim 1, wherein the medical record data includes one or more of the following data related to the patient who is undergoing the first treatment or the second treatment: medical history data of the patient, past ailments and diseases data related to the patient, data related to past treatments and procedures performed on the patient, current ailments and diseases data related to the patient, data related to current treatments and procedures being performed on the patient, diagnoses data for the patient's ailments, data related to types and amounts of medication that the patient has been prescribed in the past and is currently being prescribed, and data related to any allergies or adverse reactions to medications that the patient has.

5. The method according to claim 1, wherein the biometric data includes one or more of the following data related to the patient who is undergoing the first treatment or the second treatment: data related to the blood pressure of the patient, data related to the heartbeat rhythm of the patient, and data related to the glucose levels of the patient, data related to lipid panel of the patient.

6. The method according to claim 1, wherein the information about the first treatment includes one or more of the following data related to the patient who is undergoing the first treatment: data related to an amount of dosage of the first medication, data related to a timing of dispensation of the first medication to the patient, and data related to a manner in which the first medication is to be administered to the patient.

7. The method according to claim 1, wherein the information about second treatment includes one or more of the following data related to the patient who is undergoing the second treatment: data related to a timing of dispensation of the second medication to the patient, and data related to a manner in which the second medication is to be administered to the patient.

8. The method according to claim 1, further comprising:
implementing drug dispensing safety check and control mechanism.

9. The method according to claim 8, further comprising:
defining verifiable operation range of safety parameters or properties including drug combination and dosage concentrations related to the biometric data;
ingesting data input from various sources including health care team, electronic records, market participants and government, and transforming all external inputs to formulated logical constraints;
generating aggregated safety parameters or properties by aggregating the safety parameters or properties; and
passing the logical constraints through satisfiability modulo theory solver against the aggregated safety parameters or properties to determine whether the control mechanism is to be activated.

10. The method according to claim 9, wherein the activation of the control mechanism is based on two factor authentication or two factor validation.

11. The method according to claim 10, wherein when the control mechanism is activated, the method further comprising:
controlling dispensing amount of the first medication or the second medication.

12. The method according to claim 9, wherein when the control mechanism is activated, the method further comprising:
monitoring the biometric data of the patient in real time; and
interfacing with the patient's healthcare provider computing device and medication inventory computing device to administer the appropriate type and amount of medication to the patient that are appropriate given the patient's current health state in real time.

13. A system including a computing device configured to implement an execution of a method for integrated healthcare management and a medication dispensing device coupled to a mobile terminal, the computing device comprising:
a display screen;
a processor;
a memory;
a sensor array including an optical sensing device and a wearable device attached to the patient; and
a communication interface coupled to each of the processor, the memory, and the display screen,
wherein, when the method is being executed, the sensor array is activated to initiate measurements and biotelemetric data collection, and the processor is configured to:
generate a medical record data of a patient;
access information about a first treatment related to the medical record data of the patient;
transmit, via the optical sensing device of the sensor array, a laser pulse towards human tissue of the patient, the sensor array including a photo-acoustics system;
obtain, in real-time and via the optical sensing device of the sensor array, acoustic ultra sonic wave returned by the human tissue;
collect, in real-time via the wearable device of the sensor array, each of a blood pressure, heartbeat rhythm and glucose levels;
derive biometric data related to the first treatment based on the acoustic wave returned by the human tissue and each of the blood pressure, heartbeat rhythm and glucose levels;
process the biometric data;
determine whether the first treatment is appropriate with respect to the biometric data;
in response to the first treatment being appropriate with respect to the biometric data, output first information related to a first administration of a first medication;
in response to the first treatment not being appropriate with respect to the biometric data:
modify, by the processor and in real-time, a treatment recommendations for the patient and generate a second treatment to correspond to the derived biometric data, wherein the second treatment specifies a type, amount of dosage and frequency of dispensation of a second medication;
output second information related to a second administration of the second medication based on the determined second treatment;
provide, wirelessly, to an administration module in the mobile terminal separate from the computing device, instructions to administer the determined second treatment;
remotely perform an automated injection, via the medication dispensing device having a syringe and coupled to the mobile terminal, wherein the automated injection includes automatically and intravenously administering the second medication to the patient via the syringe inserted into the patient in response to the acoustic wave returned by the human tissue obtained by the optical sensing device and each of the blood pressure, heartbeat rhythm and glucose levels collected by the wearable device; and
after the second medication is administered to the patient, updating the medical record for the administrating of the second medication.

14. The system according to claim 13, wherein the processor is further configured to:
receive real-time feedback data corresponding to an efficacy of the first medication;
determine a modified dosage level of the first medication based on the received real-time feedback data; and
modify the first information related to the first administration of the first medication based on the determined modified dosage level of the first medication.

15. The system according to claim 13, wherein the processor is further configured to:
receive real-time feedback data corresponding to an efficacy of the second medication;
determine a modified dosage level of the second medication based on the received real-time feedback data; and
modify the second information related to the second administration of the second medication based on the determined modified dosage level of the second medication.

16. The system according to claim 13, wherein the biometric data includes one or more of the following data related to the patient who is undergoing the first treatment or the second treatment: data related to the blood pressure of the patient, data related to the heartbeat rhythm of the patient, and data related to the glucose levels of the patient, data related to lipid panel of the patient.

17. The system according to claim 13, wherein the processor is further configured to:
implement drug dispensing safety check and control mechanism.

18. The system according to claim 17, wherein the processor is further configured to:
- define verifiable operation range of safety parameters or properties including drug combination and dosage concentrations related to the biometric data;
- ingest data input from various sources including health care team, electronic records, market participants and government, and transform all external inputs to formulated logical constraints;
- generating aggregated safety parameters or properties by aggregating the safety parameters or properties; and
- pass the logical constraints through satisfiability modulo theory solver against the aggregated safety parameters or properties to determine whether the control mechanism is to be activated.

19. The system according to claim 18, wherein the activation of the control mechanism is based on two factor authentication or two factor validation.

20. A non-transitory computer readable medium configured to store instructions for integrated healthcare management implemented by a processor on a sensor-equipped computing device, wherein when executed, the instructions cause a processor to perform the following:
- generating a medical record data of a patient;
- accessing information about a first treatment related to the medical record data of the patient;
- transmitting, by an optical sensing device, a laser pulse towards human tissue of the patient, the sensor including a photo-acoustics system;
- obtaining, by the optical sensing device and in real-time, acoustic ultra sonic wave returned by the human tissue;
- collecting, via a wearable device attached to the patient and in real-time, each of a blood pressure, heartbeat rhythm and glucose levels;
- deriving, by the processor, biometric data related to the first treatment based on the acoustic wave returned by the human tissue and each of the blood pressure, heartbeat rhythm and glucose levels;
- processing the biometric data;
- determining whether the first treatment is appropriate with respect to the biometric data;
- in response to the first treatment being appropriate with respect to the biometric data, outputting first information related to a first administration of a first medication;
- in response to the first treatment not being appropriate with respect to the biometric data:
  - modifying, by the processor and in real-time, a treatment recommendations for the patient and generating a second treatment to correspond to the derived biometric data, wherein the second treatment specifies a type, amount of dosage and frequency of dispensation of a second medication;
  - outputting second information related to a second administration of a second medication based on the determined second treatment;
  - providing, wirelessly to an administration module in a mobile terminal separate from the sensor equipped computing device, instructions to administer the second treatment to the patient;
  - remotely performing an automated injection, by a medication dispensing device having a syringe and coupled to the mobile terminal, wherein the automated injection includes automatically and intravenously administering the second medication to the patient via the syringe inserted into the patient in response to the acoustic wave returned by the human tissue obtained by the optical sensing device and each of the blood pressure, heartbeat rhythm and glucose levels collected by the wearable device; and
- after the second medication is administered to the patient, updating the medical record for the administrating of the second medication.

* * * * *